US006803044B1

(12) United States Patent
Catania et al.

(10) Patent No.: US 6,803,044 B1
(45) Date of Patent: Oct. 12, 2004

(54) ANTIMICROBIAL AND ANTI-INFLAMMATORY PEPTIDES FOR USE IN HUMAN IMMUNODEFICIENCY VIRUS

(75) Inventors: Anna P. Catania, Milan (IT); James M. Lipton, Woodland Hills, CA (US)

(73) Assignee: Zengen, Inc., Woodland Hills, CA (US)

( * ) Notice: Subject to any disclaimer, the term of this patent is extended or adjusted under 35 U.S.C. 154(b) by 0 days.

(21) Appl. No.: 09/533,341

(22) Filed: Mar. 23, 2000

Related U.S. Application Data

(63) Continuation of application No. PCT/US00/06917, filed on Mar. 17, 2000.
(60) Provisional application No. 60/126,233, filed on Mar. 24, 1999, now abandoned.

(51) Int. Cl.[7] .............................................. A61K 47/00
(52) U.S. Cl. ........................ 424/278.1; 435/5; 530/331
(58) Field of Search ........................ 424/278.1, 188.1; 435/5; 530/331; 514/18, 6

(56) References Cited

U.S. PATENT DOCUMENTS

| 5,028,592 | A |   | 7/1991 | Lipton |
|---|---|---|---|---|
| 5,157,023 | A | * | 10/1992 | Lipton .......................... 514/18 |
| 5,739,111 | A |   | 4/1998 | Mahe |
| 6,001,812 | A |   | 12/1999 | Mahe |

FOREIGN PATENT DOCUMENTS

| EP | 0972 522 A1 | 1/2000 |
|---|---|---|
| FR | 2784028 | 4/2000 |
| WO | WO 93/01211 | 1/1993 |
| WO | WO/97/10838 | 3/1997 |
| WO | WO/99/58101 | 11/1999 |
| WO | PCT/US00/078446 | 3/2000 |
| WO | WO00/42856 | 7/2000 |

OTHER PUBLICATIONS

Barcellini, W., et. al., "Inhibitory Influences of α–MSH peptides on HIV–1 expression in Monocytic cells," 12th World AIDS Conference Geneva, Abstract No. 60685, Jun. 28–Jul. 3, 1998.
Catania, A., et. al., "The Neuropeptide α–MSH in HIV Infection and Other Conditions in Humans,"*Ann. N.Y. Acad. Sci.* 840: 848–856 (1998).
Wenzel, R.P. and Pfaller, M.A., "Candida Species: Emerging Hospital Bloodstream Pathogens," *Infect. Control. Hosp. Epidermiol.* 12:523–4 (1991).
Cartledge, J.D., et. al., "Clinically Significant Azole Cross–Resistance in Candida Isolates from HIV–Positive Patients with Oral Candidosis," *AIDS* 11:1839–44 (1997).
Catania, A., et. al., "α–Melanocyte Stimulating Hormone in the Modulation of Host Reactions," *Endocr. Rev.* 14, 564–576 (1993).
Catania, A., et. al., "Melanocortin Peptides Inhibit Production of Proinflammatory Cytokines in Blood of HIV–Infected Patients," *Peptides*, 19(6): 1099–1104 (1998).

Cutull, M. et. al., "Antimicrobial effects of α–MSH peptides," Journal of Leukocyte Biology 67:233–239 (2000).
Star, R.A., et. al., "Evidence of Autocrine Modulation of Macrophage Nitric Oxide Synthase by α–MSH," *Proc. Nat'l. Acad. Sci. (USA)* 92, 8015–8020 (1995).
Lipton, J.M., et. al., "Anti–inflammatory Effects of the Neuropeptide α–MSH in Acute Chronic and Systemic inflammation," *Ann. N.Y. Acad. Sci.* 741, 137–148 (1994).
Rajora, N., et.al., "α–MSH Modulates Local and Circulating tumor Necrosis Factor α in Experimental Brain Inflammation," *J. Neuroosci*, 17, 2181–2186 (1995).
Richards, D.B., et. al., "Effect of a–MSH (11–13) (lysine–proline–valine) on Fever in the Rabbit," *Peptides* 5, 815–817 (1984).
Hiltz, M. E., et. al., "Anti–inflammatory Activity of a COOH–terminal Fragment of the Neuropeptide α–MSH," *FASEB J.* 3, 2282–2284 (1989).
Gow, N.A., "Germ Tube Growth of *Candida albicans*," *Curr. Topics Med. Myco.* 8, 43–55 (1997).
Stevens, D.L., "Could Nonsteriodal Anti–inflammatory Drugs (NSAIDs) Enhance Progression of Bacterial Infections to Toxic Shock Syndrome?," *Clin. Infect. Dis.* 21, 977–80 (1997).
Capsoni, F., et. al., "Effect of Corticosteroids on Neutrophil Function: Inhibition of Antibody–dependent Cell–Mediated Cytotoxicity (ADCC)," *J. Immunopharmacol.* 5, 217–30 (1983).
Bhattacharya A., et. al., "Effect of Cyclic AMP on RNA and Protein Synthesis in *Candida albicans*," *Biochem, Biophysics. Res. Commun.*, 77: 1483–44 (1977).
Fauci, A.S., "Host Factors in the Pathogenesis of HIV–induced Disease," *Nature* 384: 529 (1996).
Holdeman, M., et. al., "Antipyretic Activity of a Potent α–MSH Analog," *Peptides* 6, 273–5 (1985).

(List continued on next page.)

*Primary Examiner*—Laurie Scheiner
*Assistant Examiner*—Jeffrey S. Parkin
(74) *Attorney, Agent, or Firm*—Perkins Coie LLP; Michael J. Wise

(57) ABSTRACT

The present invention is directed to a method and pharmaceuticals for treating HIV and secondary infection. One aspect of this invention involves the use of one or more polypeptides with an amino acid sequence including KPV, MEHFRWG, HFRWGKPV, or SYSMEHFRWGKPV for treatment of HIV. HIV is accompanied by infections, inflammation or both. In one preferred embodiment of the invention, the one or more polypeptides are used for treatment of HIV itself via medication taken orally or parentally. In another preferred embodiment of the invention, the treatment is for secondary infections arising from *Staphylococcus aureus* and *Candidia albicans* and can be taken either orally or parentally. In another preferred embodiment of the invention, treatment is carried out by local application of the polypeptides through a carrier onto the site of *S. aureus* or *C. albicans* infection.

20 Claims, 12 Drawing Sheets

OTHER PUBLICATIONS

Deeter, L.B., et. al., "Antipyretic Properties of Centrally Administered α–MSH Fragments in the Rabbit," *Peptides* 9, 1285–1288 (1989).

Hiltz, M.E., "Anti–inflammatory Activity of α–MSH (11–13) Analogs: Influences of Alterations in Stereochemistry," *Peptides* 12, 767–71 (1991).

Lipton, J.M., "Neuropeptide α–Melanocyte–Stimulating Hormone in Control of Fever, the Acute Phase Response, and Inflammation," *Neuroimmune Networks: Physiology and Diseases*, (Alan R. Liss, Inc. 1989) pp. 243–250.

Hiltz, M.E., et. al., "Alpha–MSH Peptodes Inhibit Acute inflammation and Contact Sensitivity," *Peptides*, 11:979–982 (1990).

Uehara, Y., et. al., "Carboxyl–terminal tripeptide of α–Melanocyte–Stimulating Hormone anagonizes interluekin–1–induced anorexia," *European Journal of Pharmacology*, 220: 119–122 (1992).

Mugridge, K.G., et. al., "α–Melanocyte–Stimulating Hormone reduces interleukin–1βeffects on rat stomach preparations possibly through interference with type I receptor," *European Journal of Pharmacology*, 197: 151–155 (1991).

Hiltz, M.E., et. al., "α–MSH Peptides Inhibit Acute Inflammation Induced in Mice by rIL–1β, rIL–6, rTNF–α and endogenous pyrogen but not that cause by LTB4, PAF and rIL–8," *Cytokine* 4(4):320–328 (1992).

Macaluso, A., et. al., "Antiinflammatory Influences of α–MSH molecules: Central Neurogenic and Peripheral Actions," *The Journal of Neuroscience*, 14(4): 2377–2382 (1994).

Lyson, K., et. al., "Binding of Anti–Inflammatory α–Melanocyte–Stimulating Hormone Peptides and Proinflammatory Cytokines to Receptors on Melanoma Cells," *Neuroimmunomodulation*, 1:121–126 (1994).

Ceriani, G., et. al., "Central Neurogenic Antiinflammatory Action of α–MSH: Modulation of Peripheral Inflammation Induced by Cytokines and other Mediators of Inflammation," *Neuroendocrinology*, 59:138–143 (1994).

Wong, K.Y., et. al., "A Potential Mechanism of Local Anti–inflammatory Action of Alpha–Melanocyte–Stimulating Hormone within the Brain: Modulation of Tumor Necrosis Factor–Alpha Production by Human Astrocytic Cells," *Neuroimmunomodulation*, 4:37–41 (1997).

Delgado, R., et. al., "Melanocortin peptides inhibit production of proinflammatory cytokines and nitric oxide by activated microglia," *Journal of Leukocyte Biology*, 63: 740–745 (1998).

Szalay, K.S., et. al., "Structure–activity studies with ACTH/α–MSH fragments on corticosteroid secretion of isolated zona glomerulosa and fasciculata cells," *Regulatory Peptides*, 11: 187–192 (1985).

Lichtensteiger, W., and Monnet, F., "Differential Response of Dopamine Neurons to α–Melanotropin and Analogues in Relation to Their Endocrine and Behavioral Potency," *Life Sci.* 25:2079–2087 (1979).

Eberle, A. and Schwyzer, R., "Hormone–Receptor Interactions," *Clinical Endocrinology* 5, Suppl., 41s–48s (1976).

Lipton, J.M., Modulation of Host Defense by the Neuropeptide α–MSH, *The Yale Journal of Biology and Medicines* 63: 173–182 (1990).

Hart, D.A., et. al., "*Staphylococcus aureus* Strains Differ in Their in Vitro Responsiveness to Human Urokinase: Evidence that Methicillin–Resistant Strains are Predominantly Nonresponsive to the Growth–Enhancing Effects of Urokinase," *J. Microbiol.* 42: 1024–31 (1966).

Catania, A.; et. al., "The Neuropeptide α–MSH has Specific Receptors on Neutrophils and Reduces Chemotaxis in Vitro," *Peptides*17, 675–679 (1996).

Luger, T.A., et. al., "Production of Immunosuppressing Melanotropins by Human Keratinocytes," *Ann. N.Y. Acad. Sci.* 680: 567–570 (1993).

van Nispen, J.W. and Greven, H.M., "Structure–Activity Relationships of Peptides Derived From ACTH, β–LPH and MSH With Regard To Avoidance Behavior in Rats," *Pharmac. Ther.* 16: 67–102 (1982).

Lipton, J.M., et. al., "Anti–inflammatory Actions of the Neuroimmunomodulator α–MSH," *Immunol. Today* 18, 140–145 (1997).

Thody, A.J., et.al., "MSH Peptides are Present in Mammalian Skin," *Peptides* 4, 813–815 (1983).

Fox, J. A., et al., "Immunoreactive α–Melanocyte Stimulating Hormone, Its Distribution in the Gastrointestinal Tract of Intact and Hypophysectomized Rats," *Life. Sci.* 18, 2127–2132 (1981).

Robbins Pathologic Basis of Disease $5^{th}$ ed., Saunders Co., Philadelphia (1994) p. 335–337, 354.

Airaghi, L., et. al., "Elevated concentrations of plasma α–MSH are associated with reduced disease progression in HIV–infected patients," J. Lab. Clin. Med. 133(3) 309–315 (1999).

Rajora, N., et al., "α–MSH Production Receptors and Influence on Neopterin, in a Human Monocyte/macrophage Cell Line," *J. Leukoc. Biol.* 59, 248–253 (1996).

Csata, M. et. al., "Enhancement of Candida albicans killing activity of separated human epidermal cells by alpha–melanocyte stimulating hormone," British Journal of Dermatology, 121(1) 145–147 (1989).

U.S. patent application Ser. No. 09/535,066, Lipton, filed Mar. 23, 2000.

U.S. patent application Ser. No. 60/200,287, Lipton, filed Apr. 28, 2000.

U.S. patent application Ser. No. 09/774,282, Lipton, filed Jan. 29, 2001.

U.S. patent application Ser. No. 09/828,272, Lipton, filed Mar. 23, 2000.

U.S. patent application Ser. No. 09/704,327, Lipton, filed Nov. 1, 2000.

Airaghi L. Garofalo L. Cutuli MG. Delgado R. Carlin A. Demitri MT. Badalamenti S. Graziani G. Lipton JM. Catania A. Plasma concentrations of α–melanocyte–stimulating hormone are elevated in patients on chronic haemodialysis. Nephrology Dialysis Transplantation 15:1212–1216, 2000.

Airaghi, L. Lettino M, Manfredi MG, Lipton JM, Catania A. Endogenous cytokine antagonists during myocardial ischemia and thrombolytic therapy. Am. Heart J. 130: 204–211, 1995.

Baker, et al., "Principles of Ambulatory Medicine," *Williams and Wilkins* (1982).

Baker, M., et. al., "The Relationship between Interleukin–6 and Herpes Simplex Virus Type–1: Implications for Behavior and Immunopathology," *Brain Behav. Immun.* 13(3):201–11 (1999).

Barcellini W, La Maestra L, Clerici, G, Garofalo L, Brini AT, Lipton JM, Catania A. α–MSH peptides inhibit HIV–1 expression in chronically infected promonocytic U1 cells and in acutely infected monocytes. Journal of Leukocyte Biology 68:693–699, 2000.

Bickers, D., Sun–Induced Disorders, *Emergency Medicine Clinics of North America*, 3(4): 659–663, 660 (1985).

Catania A, Airaghi L, Lipton JM. a–MSH in normal human physiology and disease states. Trends Endocrinol. Metab. 11:304–308, 2000.

Catania A, Delgado R, Airaghi L, Cutuli M, Garofalo L, Carlin A, Demitri MT, Lipton JM, α–MSH in systemic imflammation: central and peripheral actions. Annals of the New York Academy of Sciences, 885:183–187, 1999.

Catania A, Grazia M, Manfredi MG, Airaghi L, Ceriani G, Gandino A, Lipton JM. Cytokine antagonists in infectious and inflammatory disorders. Annals of the New York Academy of Sciences 741: 149–161,1994.

Catania A, Lipton JM. α–melanocyte–stimulating hormone peptides in host responses: from basic evidence to human research. Annals of the New York Academy of Sciences 680: 412–423, 1993.

Catania A, Cutuli M, Garofalo L, Airaghi L, Valenza F, Lipton JM, Gattinoni L. Plasma concentrations and anti–L–cytokine effects of α–melanocyte stimulating hormone in septic patients. Crit. Care Med. 28: 1403–1407, 2000.

Catania A, Airaghi L, Motta P, Manfredi MG, Annoni G, Pettenati G, Pettenati C, Brambilla F and Lipton JM. Cytokine antagonists in aged subjects and their relation with cellular immunity Journal of Gerontology: Biological Sciences 52A: B93–97, 1997.

Catania A, Manfredi MG, Airaghi L, Vivirito MC, Capetti A, Milazzo F, Lipton JM and Zanussi C. Plasma concentration of cytokine antagonists in patients with HIV infection. Neuroimmunomodulation 1: 42–49, 1994.

Catania A, Airaghi L, Manfredi MG, Vivirito MC, Milazzo F, Lipton JM, Zanussi C: Proopiomelanocortin–derived peptides and cytokines: relations in patients with acquired immunodeficiency syndrome. Clinical Immunology and Immunopathology 66: 73–79, 1993.

Cavello, J. and Deleo, V., Sunburn, *Dermatologic Clinics*, 4(2): 181–187, 181 (1986).

Chiao H, Foster S, Thomas R, Lipton J, and Star RA. α–MSH reduces endotoxin–induced liver inflammation. J. Clin. Invest. 97: 2038–2044, 1996.

Domk–Optiz, I., et al., "Stimulation of Macrophages by Endotoxin Results in the Reactivation of a Persistent Herpes Simplex Virus Infection," *Scand J. Immunol.* 32(2):69–75 (1990).

Fitzpatrick, et al., "Color Atlas and Synopsis of Clinical Dermatology," (1983).

Fitzpatrick, et al., Acute Effects of Ultraviolet Radiation on the Skin: The Sunburn Reaction, *Dermatology in General Medicine*, 4th Edition, 1651–1655, 1651 (1993).

Foster, J. Sunburn, *eMedicine—Online Medical Reference Textbook*, (last modified May 1, 2000), <http://emedicine.com/emerg/topic798.htm.

Galimberti D, Baron PL, Meda L, Prat E, Scarpini E, Delgado R, Catania A, Lipton JM, Scarlato G. α–MSH peptides inhibit production of nitric oxide and tumor necrosis factor–αby microglial cells activated with β–amyloid and interferon γ. Biochemical Biophysical Research Communications 263: 251–256, 1999.

"Harry's Comseticology", *Chemical Publishing*, 7$^{th}$ ed. (1982).

Huh S–K, Lipton JM and Batjer HH. The protective effects of α–melanocyte stimulating hormone on canine brainstem ischemia. Neurosurgery 40:132–139, 1997.

Ichiyama T, Sakai T, Catania A, Barsh GS, Furukawa S, Lipton JM. Systemically administered α–melanocyte–stimulating hormone peptides inhibit NF–κB activation in experimental brain inflammation. Brain Research 836: 31–37, 1999.

Ichiyama T, Zhao H, Catania A, Furukawa S, Lipton JM. α–melanocyte–stimulating hormone inhibits NF–κB activation and IαBκ degradation in human glioma cells and in experimental brain inflammation. Experimental Neurology 157:359–365, 1999.

Ichiyama T, Campbell IL, Furukawa S, Catania A, Lipton JM. Autocrine α–melanocyte–stimulating hormone inhibits NF–κB activation in human glioma cells. Journal of Neuroscience Research 58:684–689, 1999.

Ichiyama T, Okada K, Campbell IL, Furukawa S, Lipton JM. NFκB activation is inhibited in human pulmonary epithelial cells transfected with α–melanocyte–stimulating hormone vector. Peptides 21: 1473–1477, 2000.

Ichiyama T, Sakai T, Catania A, Barsh GS, Furukawa S, Lipton JM. Inhibition of peripheral NF–κB activation by central action of α–melanocyte–stimulating hormone. Journal of Neuroimmunology 99: 211–217, 1999.

Lipton JM, Catania A, Ichiyama T. Marshalling the anti–inflammatory influence of the neuroimmunomodulator α–MSH. News Physiol. Sci, 15: 192–195, 2000.

Lipton JM, Catania A. The neuropeptide α–MSH: a modulator of host reactions. Seminars in Clinical Immunology 10: 25–29, 1995.

Lipton JM, The Neuropeptide Alpha–Melanocyte–Stimulating Hormone Inhibits Experimental Arthritis in Rats, Neuroimmunomodulation 1:28–32, (1994).

Mayhall, Ten Home Remedies for Sunburn, *Seasonal Health*, (Jul. 14, 2000), <http://drkoop.com/wellness/seasonal/summer/sunburn.html>.

Noisakran S., e. al., "Lymphocytes Delay Kinetics of HSV–1 Reactivation from in vitro Explants of Latent Infected Trigeminal Ganglia," *J. Neuroimmunol.* 95(1–2):126–35 (1999).

Patel, A., et al., "Herpes Simplex Type 1 Induction of Persistent NFκB Nuclear Translocation Increases the Efficiency of Virus Replication," *Virology* 247(2):212–22 (1998).

Potts, Sunlight, Sunburn, and Sunscreens, *Postgrad. med.*, 87:52–61 (1990).

Rajora N, Boccoli G, Catania A and Lipton JM. α–MSH modulates experimental inflammatory bowel disease. Peptides 18:381–385, 1997.

Rajora N, Boccoli G, Burns D, Sharma S, Catania AP and Lipton JM. α–MSH modulates local and circulating TNF–αin experimental brain inflammation. The Journal of Neuroscience 17: 2181–86, 1997.

Remington's Pharmaceutical Sciences, *Mack Publishing Co., 18$^{th}$ ed.* (1990).

Taherzadeh S, Sharma S, Chhajlani V, Gantz I, Rajora N, Demitri MT, Kelly L, Zhao H, Catania A, Lipton JM. α–MSH and its receptors in regulation of tumor necrosis factor–αproduction by human monocyte/macrophages. Am. J. Physiol. 276: R1289–R1294, 1999.

Walev, I., et. al., "Enhancement by TNF–alpha of Reactivation and Replication of Latent Herpes Simplex Virus from Trigeminal Ganglia of Mice," *Arch Virol.* 140(6):987–92 (1995).

Watanabe T, Hiltz ME, Catania A, Lipton JM. Inhibition of IL–1β–induced peripheral inflammation by peripheral and central administration of analogs of the neuropeptide α–MSH. Brain Research Bulletin 32: 311–314, 1993.

"Vaginitis," National Institute of Child Health and Human Development—Publications On–Line (last modified Jan. 12, 2000).<www.nichd.nih.gov/publications/pubs/vagtoc.html>.

"Tampons and Asbestos, Dioxins, & Toxic Shock Syndrome," FDA Center for Devices and Radiological Health (Jul. 23, 1999), <http://www.fda.gov/cdrh/ocd/tamponsabs.html>.

Khurshid, M.A., et. al., :Staphylococcus aureus with Reduced Susceptibility to Vancomycin—Illinois, 1999, *Morbidity and Mortality Weekly Report*, 48(51): 1165–1667 (2000), <http://www.cdc.gov/epo/mmwr/preview/mmwrhtml/mm4851a1.htm>.

"Women's Health, Urinary Tract Infections: A Patient's Guide to Treatment," *AMA Health Insight, On–Line Health Information for Everyone* (last updated Oct. 30, 1998), <http://www.ama–assn.org/insight/h_focus/wom_hlth/uti/uti.htm>.

Getting, et al., POMC Gene–Derived Peptides Activate Melanocortin Type 3 Receptor on Murine Macrophages, Suppress Cytokine Release, and Inhibit Neutrophil Migration in Acute Experimental Inflammation, J. Immunol., vol. 162, No. 12, pp. 7446–7453, (1999).

Harris, et al., Alpha–melanocyte stimulating hormone (a–MSH) and melanin–concentrating hormone (MCH) stimulate phagocytosis by head kidney leucocytes of rainbow trout (Oncorhynchus mykiss) in vitro, Fish & Shellfish Immunol., vol. 8, 8:631–638 (1998).

Huang, et al., Role of central melanocortins in endotoxin–induced anorexia, Am. J. Physio (Regulatory, Integrative & Comparative Physiology, vol. 276, No. 3, pp. R864–R871 (1999).

Lipton, et al., Mechanisms of antiinflammatory action of the neuro immunomodulatory peptide alpha–MSH, Annals of the N.Y. Acad. Sci., vol. 840, pp. 373–380 (1998).

Weiss, et al., Corticotropin–peptide regulation of intracellular cyclic–AMP production in cortical neurons in primary culture, J. Neurochem. vol. 45, No. 3, pp. 869–874 (1985).

U.S. patent application Ser. No. 09/957,765, Catania et al., filed Sep. 21, 2001.

* cited by examiner

Day 6

Day 13

Day 21

Blastospores
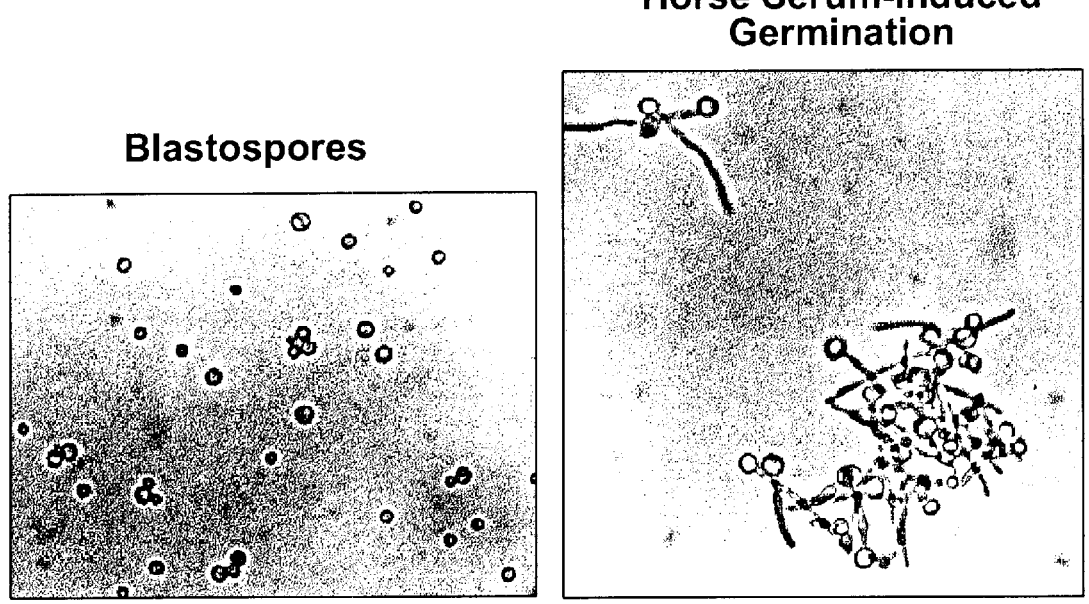
Horse Serum-Induced Germination
FIG. 12A
FIG. 12B
Effect of α-MSH (1-3) Treatment on Germination
Effect of α-MSH (11-3) Treatment on Germination
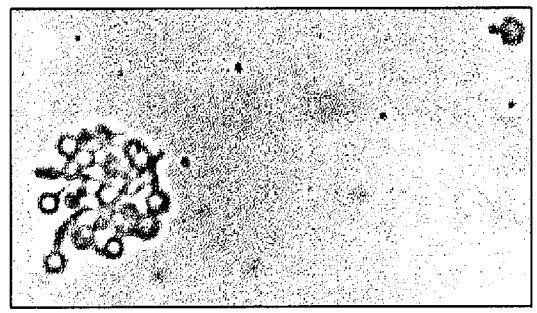
FIG. 12C
FIG. 12D

SEQUENCE LISTING

<160> NUMBER OF SEQ ID NOS: 8

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 1

Met Glu His Phe Arg Trp Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:  Synthetic
      peptide

<400> SEQUENCE: 2

His Phe Arg Trp Gly Lys Pro Val
1               5

<210> SEQ ID NO 3
<211> LENGTH: 13
<212> TYPE: PRT
<213> ORGANISM: Homo sapiens

<400> SEQUENCE: 3

Ser Tyr Ser Met Glu His Phe Arg Trp Gly Lys Pro Val
1               5                   10

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence:  The base
      peptide for a KPV dimer

<400> SEQUENCE: 4

Cys Lys Pro Val
1

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence:  Synthetic
      oligonucleotide

<400> SEQUENCE: 5
gatccaaggg gactttccgc tggggacttt ccatg                              35

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence:  Synthetic
      oligonucleotide

<400> SEQUENCE: 6
gatccatgga aagtccccag cggaaagtcc ccttg                              35

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:  Synthetic
      primer
```

```
-continued

<400> SEQUENCE: 7
gccaccatgc caagaacc                                                        18

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 8
atagccagga agaagacca                                                       19
```

ANTIMICROBIAL AND ANTI-INFLAMMATORY PEPTIDES FOR USE IN HUMAN IMMUNODEFICIENCY VIRUS

CROSS REFERENCE TO RELATED APPLICATION

This application is a continuation of commonly owned PCT Patent Application Serial No. PCT/US00/06917 filed Mar. 17, 2000, which claims the priority of U.S. patent application Ser. No. 60/126,233 filed Mar. 24, 1999, now abandoned.

BACKGROUND OF THE INVENTION

The present invention relates to a new pharmaceutical composition and method for use as a treatment of human immunodeficiency virus ("HIV"), as well as for secondary microbial infections and inflammation in persons with HIV. More particularly, this invention relates to a tripeptide sequence contained in alpha-melanocyte stimulating hormone ("alpha-MSH"), which has been identified as an antiviral, antibacterial, antifungal and anti-inflammatory agent.

HIV is a virus that weakens the immune system through destruction of lymphocytes. Because thousands of people die each year from HIV, the need for treatment of the virus, as well as secondary infections, is significant. HIV is considered to be a member of the lentivirus family of animal retroviruses on the basis of genomic sequence homologies, morphology and life cycle. Lentiviruses are capable of long-term latent infection, infection of cells or short-term cytopathic effects, and they all produce slowly progressive, fatal diseases. Both humoral and cell-mediated immune responses specific for a wide variety of HIV gene products have been observed in HIV-infected patients. Given the high fatality rate among HIV-infected individuals, it is clear that these immune responses to the viruses do not confer adequate protection. Because of the complex biology of HIV, the clinical manifestations of infection are quite variable. Persons with HIV frequently become infected with *Staphylococcus aureus* and *Candida albicans*.

*S. aureus* organisms are pyogenic, nonmotile, gram-positive cocci that tend form grape-like clusters. Staphylococci cause a myriad of skin lesions, such as boils, carbuncles, impetigo and scalded skin. Staphylococci also cause pharymgitis, pneumonia, endocarditis, food poisoning and toxic shock syndrome. *S. aureus* is the major cause of infection of patients with severe burns and surgical wounds and is second only to *E. coli* as a cause of hospital-acquired infections.

*S. aureus* possesses a multitude of virulence factors, which includes surface proteins involved in adherence to host cells, secreted enzymes that degrade host proteins, and secreted toxins that damage host cells. *S. aureus* has, on its surface, receptors for fibrinogen, fibronectin, and vitronectin and uses these molecules as a bridge to bind to host endothelial cells.

*S. aureus* has a laminin receptor which is similar to metastatic tumor cells and allows bacteria to bind to host extracellular matrix proteins and invade host tissues.

Staphylococci infecting prosthetic valves and catheters have an exopolysaccharide capsule that allows them to attach to the artificial materials and to resist host cell phagocytosis.

The lipase of *S. aureus* degrades lipids on the skin surface, and its expression is correlated with the ability of the bacteria to produce skin abscesses.

*S. aureus* produces multiple hemolytic toxins, including alpha toxin, which is a pore-forming protein that intercalates into the plasma membrane of host cells and depolarizes them; betatoxin, a sphingomyelinase; and delta-toxin, which is an anphipathic (detergent-like) peptide.

*S. aureus* enterotoxins are associated with food poisoning and appear to act by stimulating emetic receptors in the abdominal viscera to cause vomiting and diarrhea. In addition, *S. aureus* enterotoxins are superantigens. They bind to macrophage major histocompatibility complex (MHC) class II molecules at a conserved site away from the hypervariable groove and then to the site of the T-cell receptor beta chain, rather than to its variable face that recognizes conventionally processed antigens bound to the MHC. This leads to massive stimulation of host T cells and release of cytokines, which mediate the systemic effects of *S. aureus* enterotoxin.

Exfoliative toxins of *S. aureus* are associated with the staphylococcal scalded-skin syndrome, in which cells in the granular layer of the epidermis detach from each other and form skin blisters.

*Candida albicans* is the most common human fungal infection. *C. albicans* is part of the normal floor of the skin, mouth, and GI tract. *C. albicans* infections vary from superficial lesions in healthy persons to disseminated infections in neutropenic patients.

*Candida* grow as yeast forms which are tandem arrays of elongated forms without hyphae (pseudohyphae), and true hyphae with septae. All may be mixed together in the same tissue, and all are stained with Gram, periodic acid-Schiff, or methenamine silver. *Candida* grows best on warm, moist surfaces and so frequently causes vaginitis (particularly during pregnancy), diaper rash, and oral thrush. Dishwashers, diabetics, and burn patients are also particularly susceptible to superficial *Candidiasis*. Chronic *Mucocutaneous candidiasis* occurs in persons with AIDS, in individuals with inherited or iatrogenic defects in T cell-mediated immunity, and in persons with polyendocrine deficiencies (hypoparathyroidism, hypoadrenalism, and hypothyroidism). Severe disseminated *candidiasis* is associated with neutropenia secondary to chronic granulomatous disease, leukemia, anticancer therapy, or immunosuppression after transplantation. *Candida* is directly introduced into the blood by intravenous lines, catheters, peritoneal dialysis, cardiac surgery, or intravenous drug abuse. Although the course of candidal sepsis is less rampant than that of bacterial sepsis, disseminated *Candida* eventually causes shock and DIC.

*Candida* has numerous molecules on its surface that mediate its adherence to host tissues, including (1) a receptor homologous to the human CR3 integrin, which binds RGD groups on C3bi, fibrinogen, fibronectin, and laminin; (2) a lectin that binds sugars on epithelial cells; and (3) mannose-containing proteins that bind to lectin-like molecules on epithelial cells. Other virulence-associated factors include a secreted aspartyl proteinase, which may be involved in tissue invasion by degrading extracellular matrix proteins, and secreted adenosine, which blocks neutrophil oxygen radical production and degranulation.

SUMMARY OF THE INVENTION

The present invention is directed to a method and pharmaceuticals for treating HIV and secondary infection. One aspect of this invention involves the use of one or more polypeptides with an amino acid sequence including KPV, MEHFRWG (SEQ ID NO: 1), HFRWGKPV (SEQ ID NO:

2), or SYSMEHFRWGKPV (SEQ ID NO: 3) for treatment of HIV. HIV is accompanied by infections, inflammation or both. In one preferred embodiment of the invention, the one or more polypeptides are used for treatment of HIV itself via medication taken orally or parenterally. In another preferred embodiment of the invention, the treatment is for secondary infections arising from *Staphylococcus aureus* and *Candidia albicans* and can be taken either orally or parentally. In another preferred embodiment of the invention, treatment is carried out by local application of the polypeptides through a carrier onto the site of *S. aureus* or *C. albicans* infection.

BRIEF DESCRIPTION OF THE DRAWINGS

The accompanying figures are incorporated into and form a part of the application to provide illustrative examples of the present invention and to explain the principles of the invention. The figures of the drawings are only for purposes of illustrating preferred and alternate embodiments of how the invention can be made and used. It is to be understood, of course, that the drawing is intended to represent and illustrate the concepts of the invention. The figures of the drawing are not to be construed as limiting the invention to only the illustrated and described examples. Various advantages and features of the present invention will be apparent from a consideration of the written specification and the accompanying figures of the drawing wherein.

In this and following figures bars represent the mean±SE.

$*p<0.05;**p<0.0$

Figure 3A:
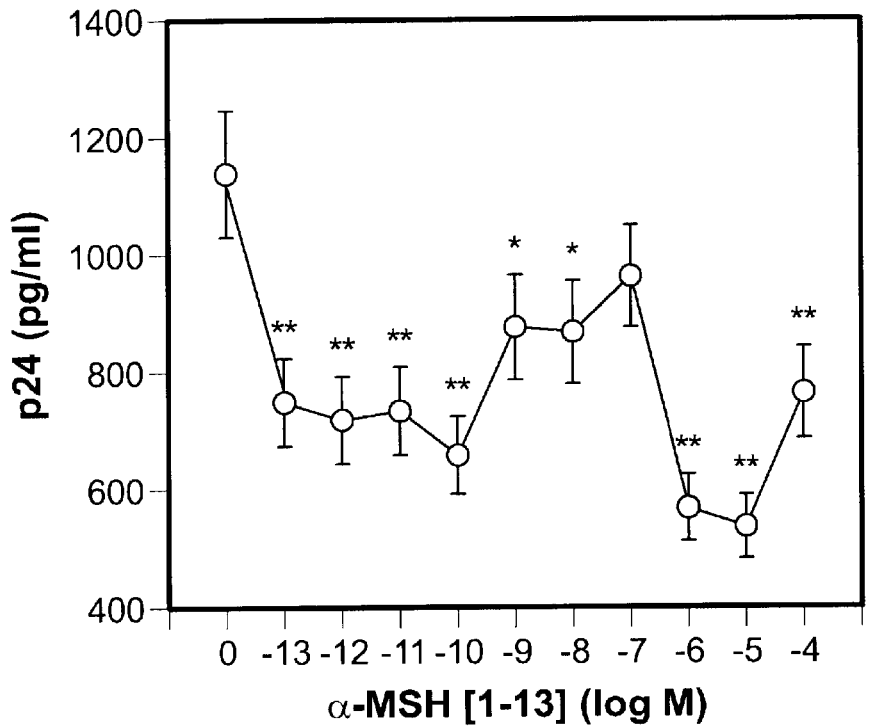
Figure 3B:
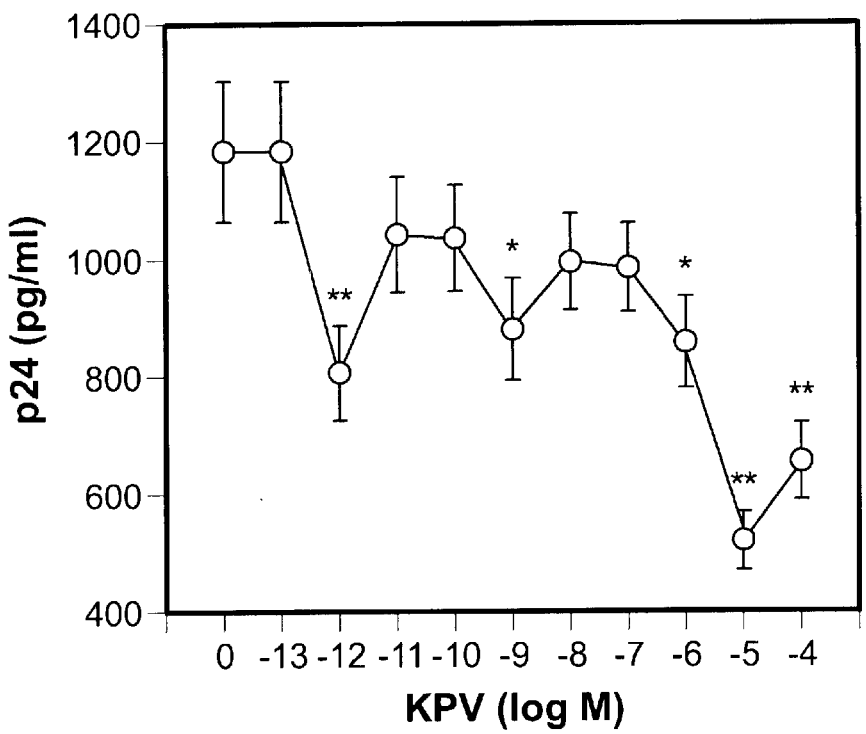

FIG. 3. Effect of treatment with α-MSH[1–13] or KPV on p24 release by TNF-α stimulated U1 cells. Both α-MSH peptides inhibited p24 release over a broad spectrum of concentrations.

Figure 4B:
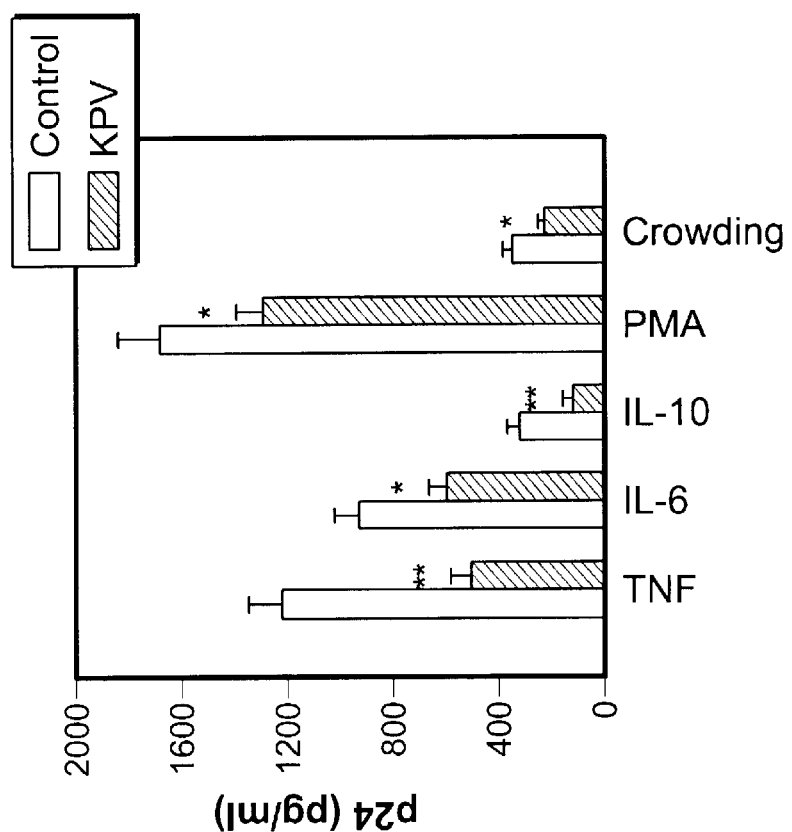
Figure 4A:
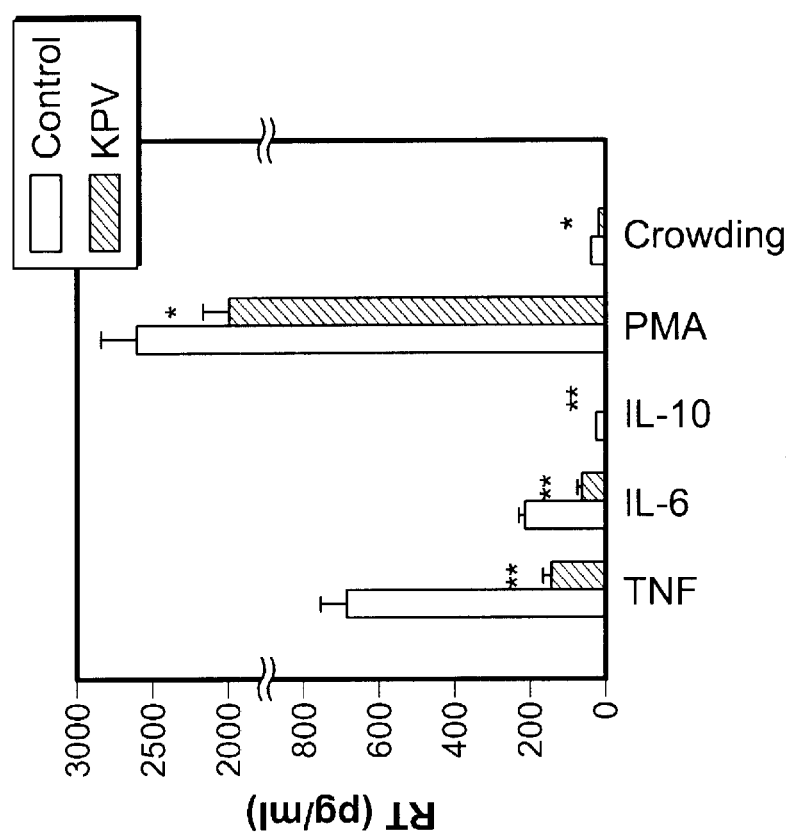

FIG. 4. Effect of KPV on RT and p24 release by stimulated U1 cells. Treatment with KPV ($10^{-5}$ M) inhibited RT and p24 release from U1 cells exposed to different stimuli.

Figure 5A:
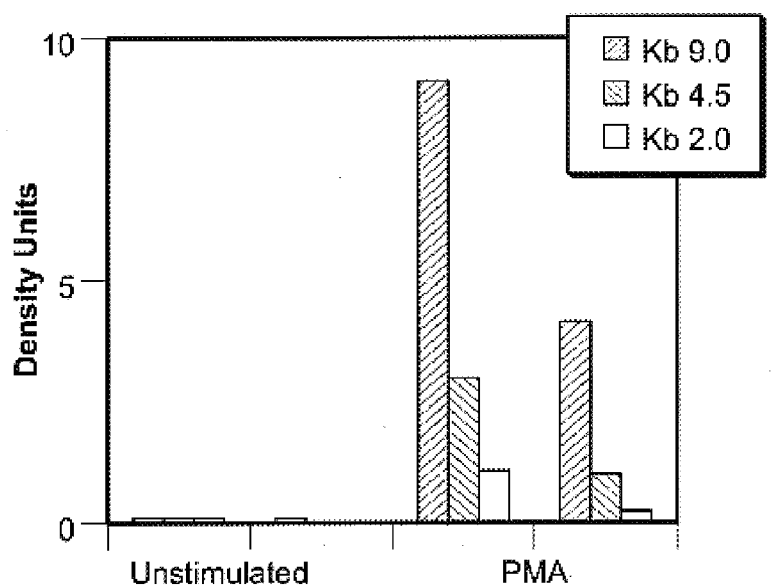
Figure 5B:
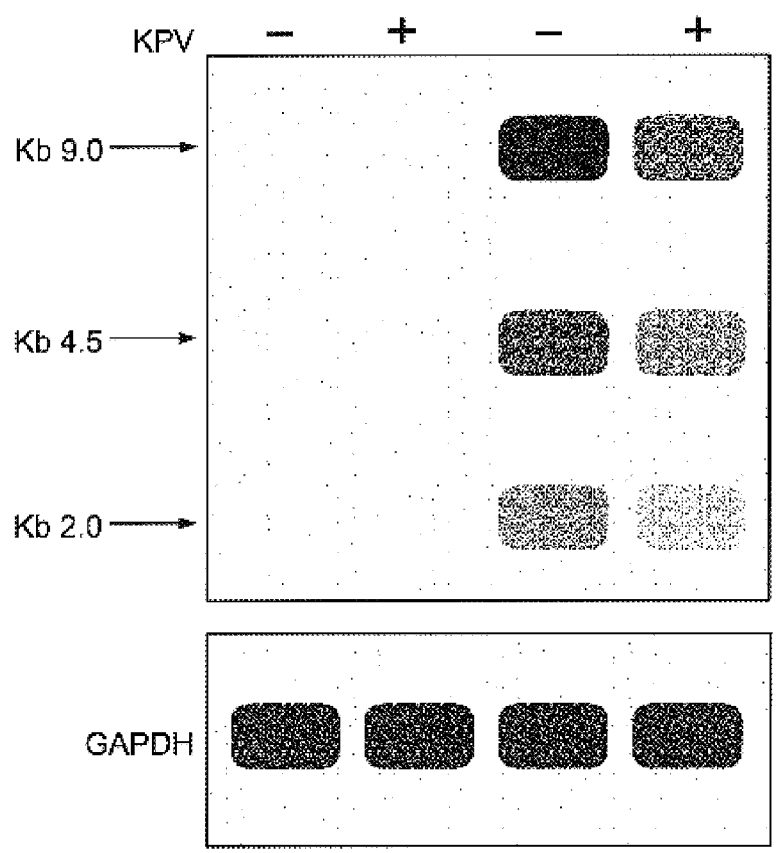

FIG. 5. Effect of treatment with KPV on HIV RNA in resting and PMA-stimulated U1 cells. Addition of KPV ($10^{-5}$M) reduced by approximately 50% both spliced and unspliced HIV-1 RNA in PMA-stimulated U1 cells.

Figure 6A:
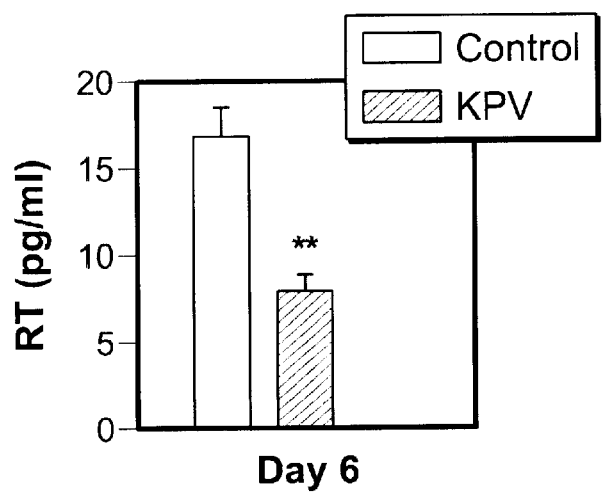
Figure 6B:
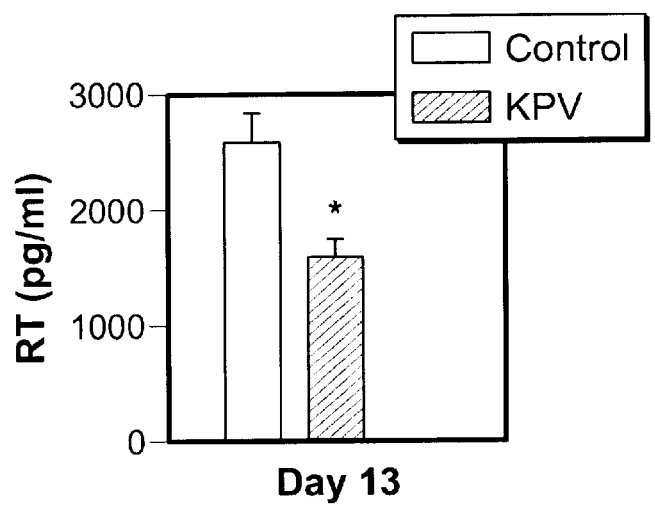
Figure 6C:
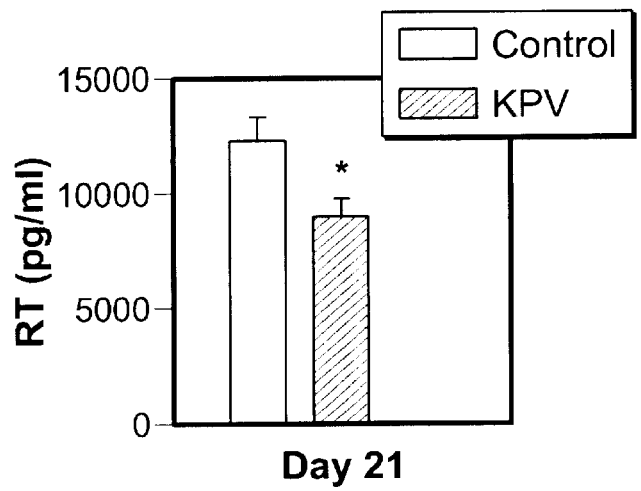

FIG. 6. Effect of treatment with KPV on HIV replication in acutely infected MDM. Treatment with tripeptide ($10^{-5}$M) significantly inhibited RT release from acutely HIV-infected MDM. Inhibitory effect was more pronounced on day 6 ($p<0.01$) but was still statistically significant on day 13 and 21 ($p<0.05$).

Figure 7A:
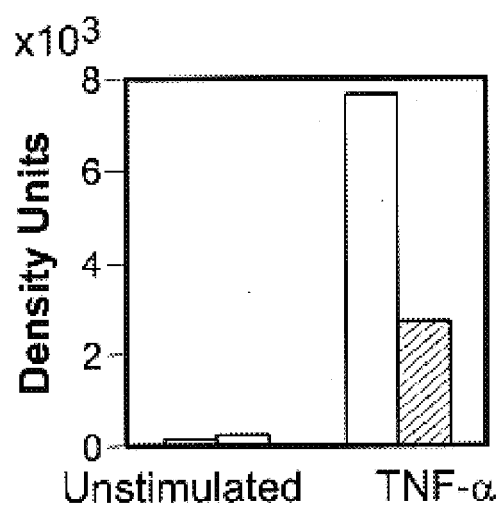
Figure 7B:
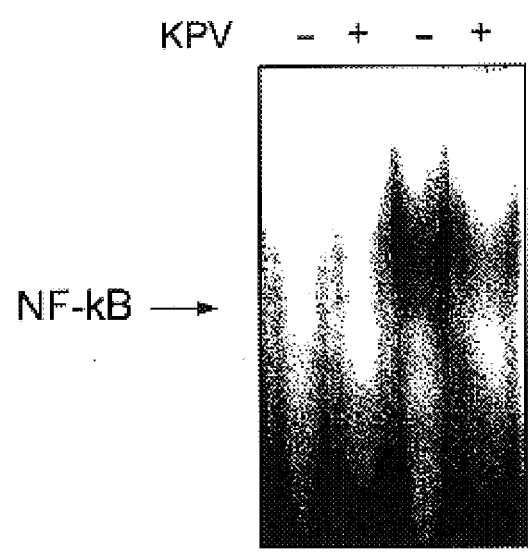

FIG. 7. Effect of treatment with KPV on NF-κB activation. KPV($10^{-5}$M) markedly reduced NF-κB activation induced by TNF-α in U1 cells. There was no change in NF-κB activation in resting cells treated with the tripeptide.

Figure 8:
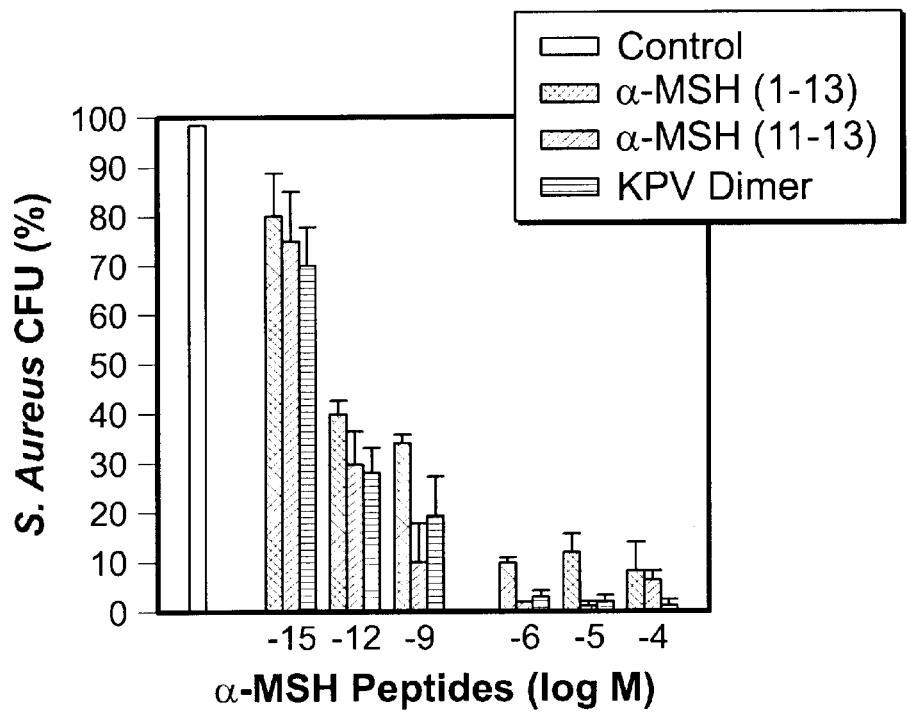

FIG. 8 shows the effect of α-MSH (1–13) and (11–13) and the "KPV dimer" on *S. aureus* colony forming units ("CFU") compared to controls. All three molecules significantly decreased *S. aureus* colony forming units over a broad range of peptide concentrations.

Figure 9:
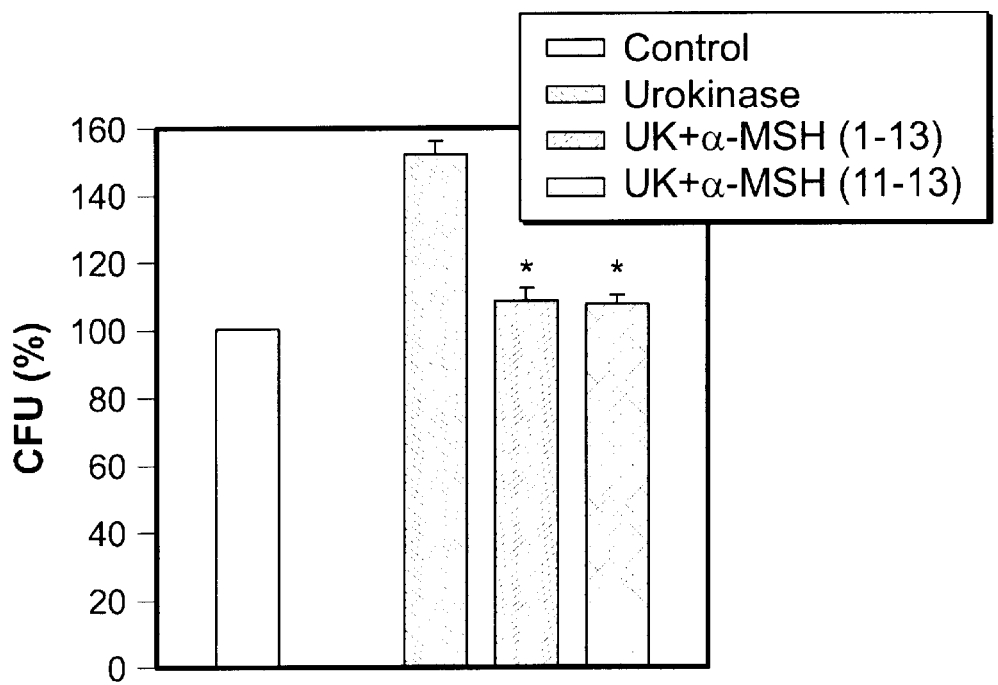

FIG. 9 shows that treatment with urokinase increases *S. aureus* colony formation, but that the addition of α-MSH (1–13) or (11–13) significantly inhibited this urokinase-enhancing effect.

$*p<0.001$ vs. urokinase alone.

Figure 10:
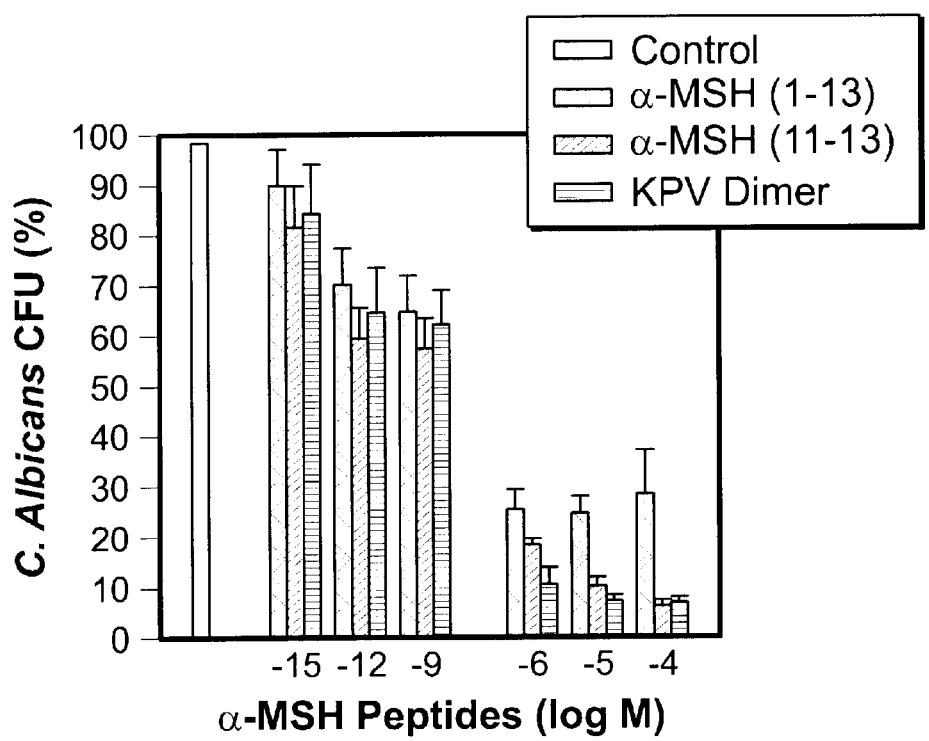

FIG. 10 shows the effect of α-MSH (1–13) and (11–13) and the "KPV dimer" on *C. albicans* colony forming units ("CFU") compared to controls. All three molecules significantly decreased *C. albicans* colony forming units over a broad range of peptide concentrations.

Figure 11:
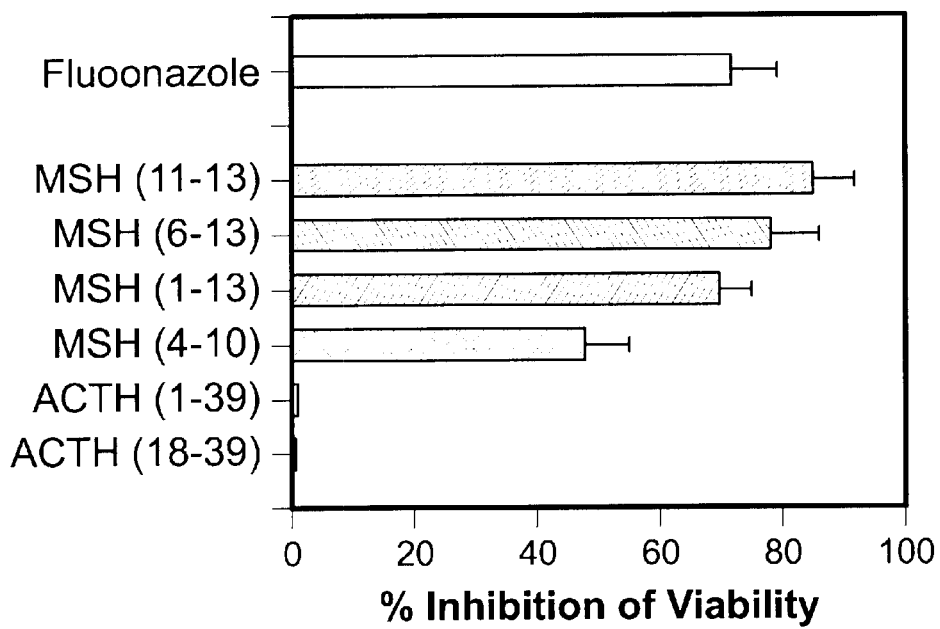

FIG. 11 shows a comparison of candidacidal activity of certain melanocortin peptides and fluconazole (all $10^{-6}$M). The most effective of the melanocortin peptides were those including the C-terminal amino acid sequence of α-MSH, for example, α-MSH (1–13), (6–13), and (11–13).

FIG. 12A shows untreated germination of *C. albicans*, i.e. blastospores.

FIG. 12B shows horse serum-induced termination of *C. albicans*.

FIG. 12C shows the effect of α-MSH (1–13) treatment on germination of *C. albicans*.

FIG. 12D shows the effect of α-MSH (11–13) treatment on germination of *C. albicans*.

Figure 13:
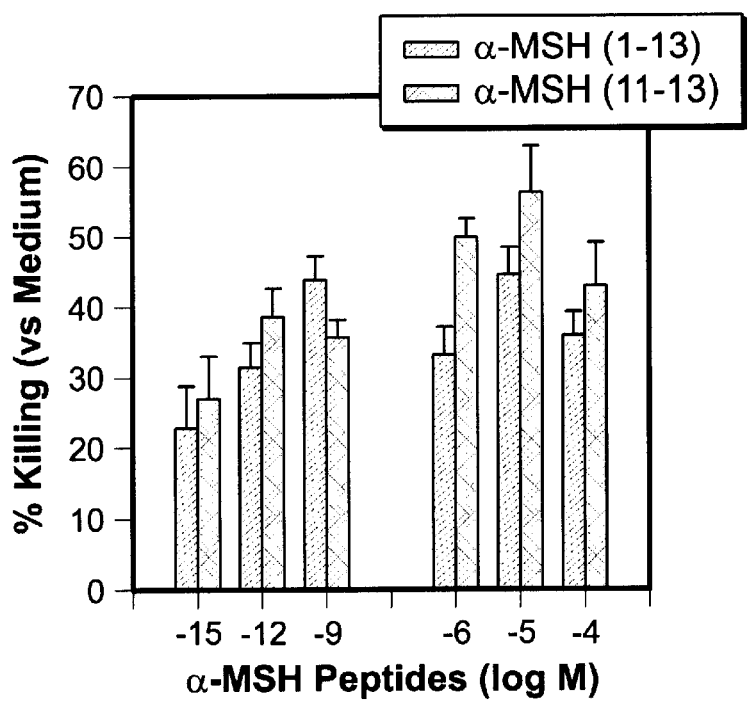

FIG. 13 shows the effect of α-MSH (1–13) and (11–13) on *C. albicans* killing by human neutrophils. Values are expressed as percent increase in killing vs. medium alone. Scores are means—SEM.

Figure 14:
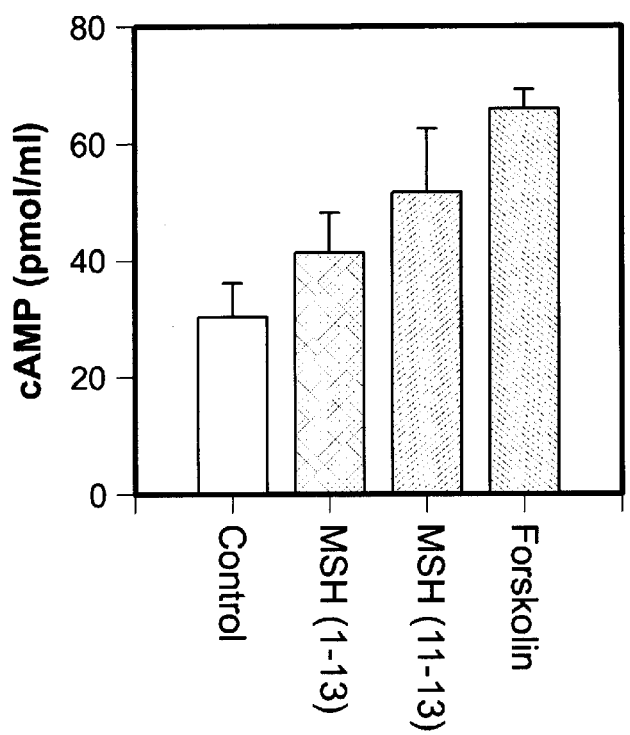

FIG. 14 shows the effect of α-MSH (1–1 3), (11–13), and forskolin on cAMP content of *C. albicans*.

Figure 15:
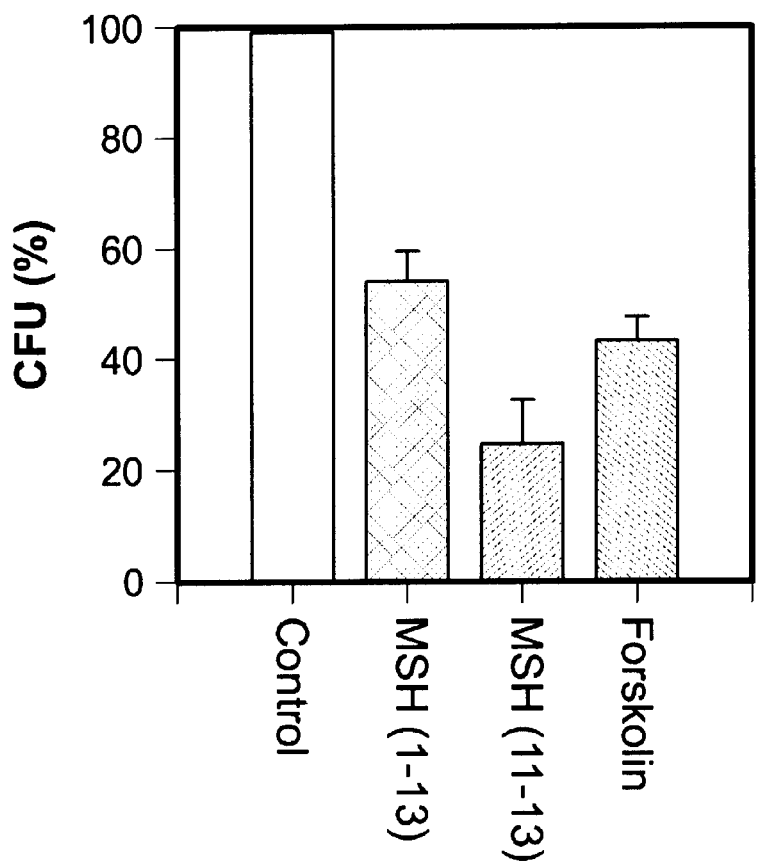

FIG. 15 shows the inhibitory effect of α-MSH (1–13), (11–13), and forskolin on *C. albicans* colony forming units.

Figure 16:
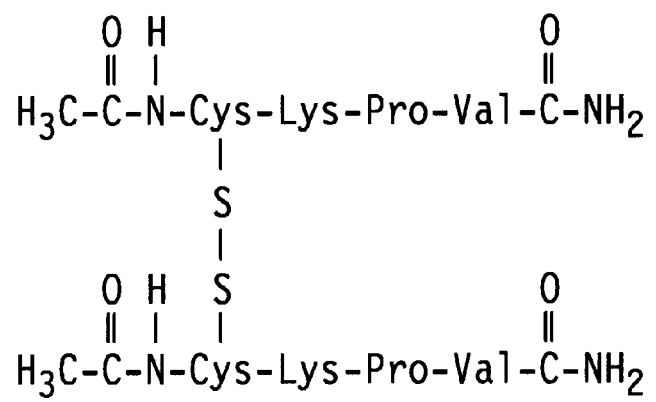

FIG. 16 shows a representation of the chemical structure for the amino acid sequence VPKCCKPV (SEQ ID NO: 4), knowm as the "KPV dimer."

DETAILED DESCRIPTION OF THE INVENTION

Discovery of effective antiviral molecules has greatly improved treatment of patients with HIV infection. However, elevated cost of antiviral drugs, emergence of resistant viral strains, and relapse after treatment remain unsolved problems. Therefore, therapies that reinforce specific anti-HIV treatments are actively sought. Because HIV replication is largely dependent on the state of activation of infected cells, drugs that reduce promoting effects of activation on viral replication are beneficial in association with antiviral molecules targeting HIV genes. Adjunctive molecules should be of low toxicity, low cost, and should not induce tolerance over long term treatment. The endogenous anti-inflammatory peptide α-melanocyte stimulating hormone (α-MSH) has many of these characteristics and is effective in HIV-infected cells, so it is a beneficial adjunctive therapy.

α-MSH (SYSMEHFRWGKPV) (SEQ ID NO: 3) is a pro-opiomelanocortin (POMC)-derived tridecapeptide with potent antipyretic and anti-inflamnmatory influences. The C-terminal tripeptide of α-MSH, KPV exerts anti-inflammatory effects in vitro and in animal models of inflammation, that are similar to those of the entire 1–13 sequence. Therefore, KPV is considered the anti-inflammatory "message sequence" of the peptide. Five G-protein-linked melanocortin receptors (MC-1R through MC-5R) have been isolated and cloned. They bind α-MSH and other melanocortin peptides such as ACTH with different affinities; MC-R are expressed in the brain and in peripheral tissues. The precursor of α-MSH, POMC, is widely expressed in tissues. However, there are distinct regional differences in expression and post-translational processing and certain cells produce, constitutively or under appropriate stimulation, greater amounts of α-MSH. α-MSH occurs in high concentrations in barrier organs such as the gut and the skin. Activated macrophages and microglia likewise produce substantial amounts of α-MSH and there is evidence that the peptide has an autocrine anti-inflammatory influence in these cells that express melanocortin receptors. The anti-inflammatory effects of α-MSH are exerted partly via inhibition of certain inflammatory mediators, such as cytokines and nitric oxide, likely through inhibition of the transcription factor NF-κB.

Recent research has shown that, in addition to its anti-inflammatory influences, α-MSH has antimicrobial activity. Anticytokine and antimicrobial effects of α-MSH show that the peptide has anti-HIV properties. α-MSH and its C-terminal tripeptide KPV reduce HIV expression in infected cells. Research involving the invention deterniined: 1) production of α-MSH and autocrine effects of the peptide on HIV expression in the chronically HIV-1 infected U1 clone; and 2) influence of α-MSH treatment on IRV expression in chronically and acutely infected monocytes.

METHODS

I. HIV

Peptides

α-MSH 1–13 SYSMEHFRWGKPV (SEQ ID NO: 3) and (11–13) KPV, both acetylated and amidated, were used.

Cell Cultures and Treatments

The chronically HIV-1 infected promonocytic U1 cell line was maintained in complete culture medium (RPMI 1640 supplemented with 10 mM Hepes), 2 mM L-glutamine (Sigma-Aldrich), 10% heat-inactivated FCS (HyClone Laboratories, Logan, Utah, USA), penicillin at 100 units/mL and streptomycin at 100 μg/mL (Gibco Laboratories, Grand Island, N.Y.) in log phase of growth. Pilot experiments were performed to determine optimal cell density, stimuli concentration, and kinetics of HIV-1 p24 antigen production using our culture conditions. Before use, cells were washed three times with HBSS (Gibco) to remove extracellular virus. Cells were plated onto 24-well flat-bottomed plates at a concentration of 2×10/mL (final volume 1 mL) with medium alone or plus TNF-α (10 ng/mL (R&D Systems, Oxford, England, UK) in the presence or absence of α-MSH [1–13] or KPV in concentrations from $10^{-13}$ to $10^{-4}$ M. In further experiments, KPV was added in the $10^{-5}$ M concentration to U1 cells stimulated with TNF-α (10 ng/mL), IL-6 (20 ng/mL), IL-10 (20 ng ImL (R&D Systems) or PMA (1 ng/mL) (Sigma-Aldrich Chemicals, St. Louis, Mo., USA). Supernatants were removed by centrifugation after 48 hr incubation at 37° C. in 5% $CO_2$, and stored at −80° C. In crowding experiments, U1 cells were seeded at the density of $2\times10^5$ mL and maintained in culture at 37° C. in 5% $CO_2$ without change of medium for 7 days. KPV (10–5M), or an equal volume of medium, were added on day 1. In all experiments each condition was tested in triplicate.

Endogenous Production and Immunoneutralization of α-MSH

α-MSH production was determined in cell free supernatants of U1 cells seeded at the density of $2\times10^5$ mL and maintained in culture at 37° C. in 5% $CO_2$ for 48 h in presence of medium or PMA (1 ng/ml). In immunoneutralization experimnents, α-MSH produced by U1 cells was blocked with an affinity purified rabbit-anti-α-MSH antibody (Euro-Diagnostica, Malmö, Sweden) diluted 1:250 with medium. Control antibody was a rabbit IgG at the same dilution. Cells ($2\times10^5$/mL) treated with the anti-α-MSH or the control antibody were coincubated with medium or PMA (1 ng/ml). After 48 h incubation at 37° C., supernatants were separated and tested for p24 antigen release. In crowding experiments, performed as described above, the anti-α-MSH antibody or the control IgG were added on day 1 and the supernatants were harvested on day 7.

Northern Blot for HIV-1

To determine the influence of KPV on HIV-RNA expression, $20\times10^6$ U1 cells (at a density of $2\times10^5$/mL in complete medium) were stimulated for 24 h with PMA (1 ng/mL) in the presence or absence of KPV $10^{-5}$M. Total RNA was extracted by the guanidine thiocyapate phenol method using an RNA isolation kit (Tripure, Boehringer Mannheim, Indianapolis, Ind.), following the manufacturer's instructions. Ten μg of total RNA were separated by 0.8% agarose/formaldehyde gel electrophoresis and transferred onto nylon membrane. The filters were baked and hybridized for 18 hr with $\alpha^{32}$ P-labeled HIV-full length probe (kind gift of L. Turchetto and E. Vicenzi, S. Raffaele Hospital, Milan, Italy). The radiolabelling reaction was performed using a DNA labelling kit (Ready-to-go, Pharmacia Biotech, San Francisco, Calif.). Filters were washed and exposed to X-ray film for 5 days. The labeled probe was removed by washing at 80° C. in 0.1×SSC containing 0.1% sodium dodecyl sulphate and then rehybridized witb $\alpha^{32}$ P-labeled glyceraldehyde-3-phosphate dehydrogenase (GAPDH) cDNA probe. Densitometric analysis was performed using ImageMaster™ VDS 3.0 software (Pharmacia Biotech) and results were expressed as density units.

Electrophoretic Mobility Shift Assay (EMSA)

For determination of NF-κB activity, nuclear extracts were prepared from $20\times10^6$ U1 cells ($2\times10^5$/mL in complete medium) stimulated for 4 h with TNF-$\alpha^{32}$ (20 ng/mL) in the presence or absence of $10^5$ M KPV. Cells were washed once with cold PBS, and twice with buffer A (10 mM Hepes pH 7.9, 1.5 mM $MgCl_2$, 10 mM KCl, 0.5 mM phenylmethylsulfonyl fluoride [PMSF; Boehringer Mannheim] and 0.5 mM dithiothreitol (DTT) [Sigma-Aldrich]), centrifuged and incubated for 10 min on ice in buffer A plus 0.1% NP-40 (Sigma-Aldrich). The supernatants were removed and the nuclear pellets resuspended in 15 μl of buffer C (20 mM Hepes pH 7.9, 1.5 mM $MgCl_2$, 0.42 M KCl, 0.2 mM EDTA, 25% glycerol, 0.5 mM PMSF and 0.5 mM DTT), incubated for 15 min on ice, mixed and centrifuged. The supernatants were diluted with 75 μl of modified buffer D (20 mM Hepes pH 7.9, 0.05 mM KC1, 0.2 mM EDTA, 20% glycerol, 0.5 mM PMSF and 0.5 mM DTT) and stored at −80° C. The binding reaction was carried out with 10 μg of nuclear extract protein and 0.5 ng of $\alpha^{32}$ P-labeled NF-κB (30,000 cpm/μl) or AP1 consensus in buffer A⁻(12 mM Tris-HCl pH 7.8, 60 mM KCl, 0.2 mM EDTA, 0.3 mM DTT), plus 10% glycerol, 2 μg/mL bovine serum albumine (BSA, Sigma-Aldrich) and 1 μg/mL sDNA (Pharmacia Biotech), for 15 min at room temperature. The oligonucleotides for NF-κB used in these studies were: + GAT CCA AGG GGA CTT TCC GCT GGG GAC TTT CCA TG, (SEQ ID NO: 5) and − GAT CCA TGG AAA GTC CCC AGC GGA AAG TCC CCT TG (SEQ ID NO: 6). Each oligonucleotide was annealed to its complementary strand and end-labeled with $\alpha^{32}$P-γ-ATP (Amersharm Corp., Arlington Heights, Ill.) using polynucleotide kinase (T4, New England Biolabs). For determination of specific bands, nuclear extracts were first incubated with 100-fold excess unlabeled probe for 5 min before incubation with the labeled probe. The mixtures were run on a 5% (30:1) acrylamide gel in 1× Tris-Borate-EDTA (TBE). Gels were dried and exposed to film for autoradiography (3 days).

MC-IR Gene Expression

U1 cells were seeded in T25 flasks at density of $2 \times 10^5$ cells/mL and incubated with medium alone or PMA (1 ng/mL) for 24 h. Cells were then washed with cold PBS and total RNA was extracted as described above. The amount of total RNA was determined photometrically at 260 nm. Extracted RNA was used for reverse transcription and PCR amplification. Because MC-1 receptor gene lacks introns, genomic DNA was digested with DNAse for 30 min at 37° C. DNAse was inactivated by phenol-chloroform extraction. One microgram of total RNA was reverse transcribed using random primers and AMV RT (Boehringer Mannheim). In some tubes the RT was omitted to control for amplification from contaminating cDNA or genomic DNA. Fragments derived from the coding regions of human MC-1 cDNAs were amplified using primers synthesized commercially (Genset SA, France). The MC-IR forward primer was GCC ACC ATG CCA AGA ACC (SEQ ID NO: 7) the reverse primer was ATA GCC AGG AAG AAG ACCA (SEQ ID NO: 8) (all shown as 5' to 3'). PCR mixture contained the following: 0.8 $\mu$M of each primer, 1.5 mM $MgCl_2$, 200 $\mu$M dNTPs, 10× reaction buffer and 2 units of Taq DNA polymerase/reaction (Amply Taq; Perkin Elmer Italiana, Monza, Italy). To minimize nonspecific amplification, the Taq DNA polymerase was added to PCR tubes prewarmed to 80° C. The PCR temeprature profile consisted of 35 cycles of 94° C. for 45 sec (denaturing), 57° C. for 45 sec (annealing), and 72° C. for 1 min, followed by a 7-min final extension at 72° C. The PCR products were separated on 2% agarose, stained with ethidium bromide and photographed under UV light.

p24 and RT Determinations p24 antigen release (Cellular Products Inc. Buffalo, N.Y., USA) and reverse transcriptase (ELISA Retrosys RT assay, Innovagen, Lund, Sweden) were determined using commercial ELISA kits.

α-MSH Measurement

α-MSH was measured with a competitive radioimmunoassay kit (Euro-Diagnostica, Malmö, Sweden). The detection limit was 0.9 pmol/mL.

Acute Infection of Monocyte Derived Macromhayes (MDM)

Human peripheral blood mononuclear cells (PBMCs) were isolated from normal donors by Ficoll-Hypaque density gradient centrifugation. Monocytes were isolated by Percoll gradient separation and allowed to differentiate into macrophages (MDM) in complete medium RPMI plus 20% FCS in 24-well tissue culture plates at $10^6$ cells/mL for 7-days. MDM were infected with monocytotropic HIV-$1_{Ba-L}$ strain (1:10) overnight. The undiluted viral stock contained $10^7$ infectious Units/mL. After 24 h, MDM were washed and resuspended in complete medium, replaced 3 times/week, for 3 weeks. RT activity was measured weekly post-infection. $10^{-5}$M KPV was added at the time of HIV infection and daily until harvest.

Statistical Analysis

All values are given as mean±SE. Comparison of group means was performed using ANOVA of ranks followed by Dunn's test for specific comparisons. Two sample comparisons were performed using Mann-Whitney rank sum test. Probability values less than 0.05 were considered significant.

Results

Figure 1:
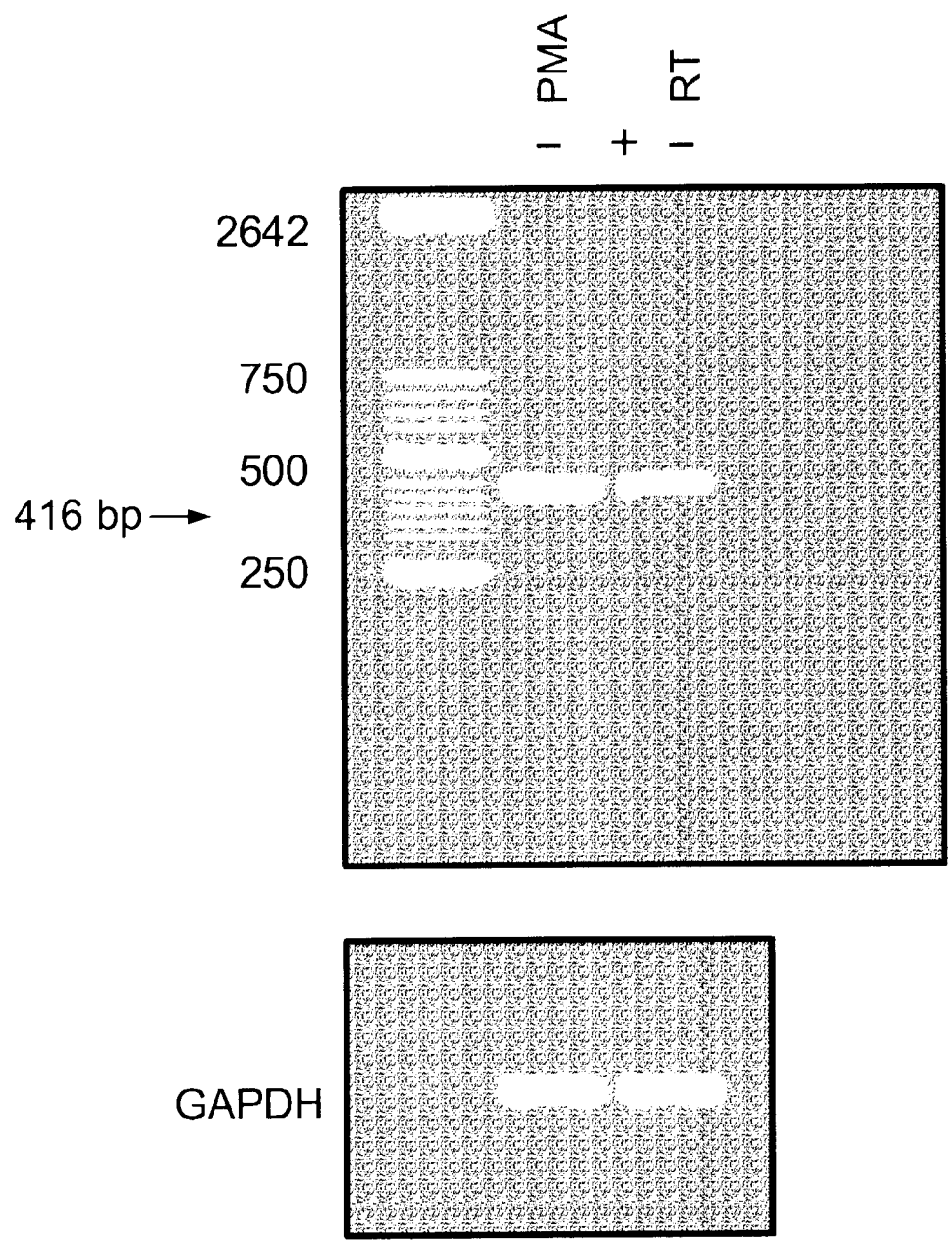
FIG. 1, MC-1R expression in U1 cells. In both resting and PMA-stimulated cells a PCR product specific for MC-1R with the expected length of 416 bp was detected.
Figure 2C:
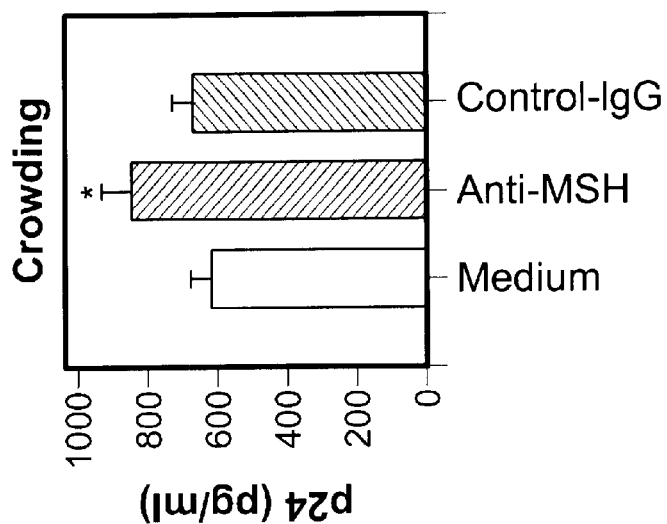
FIG. 2. Effect of immunoneutralization of endogenous α-MSH on p24 release by U1 cells. Immunoneutralization of endogenous α-MSH increased p24 release by U1 cells in resting and crowding conditions, and after stimulation with PMA.
Figure 2B:
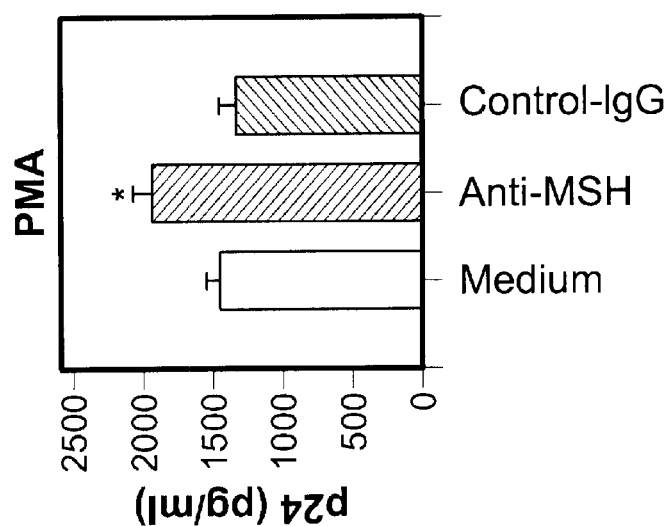
Figure 2A:
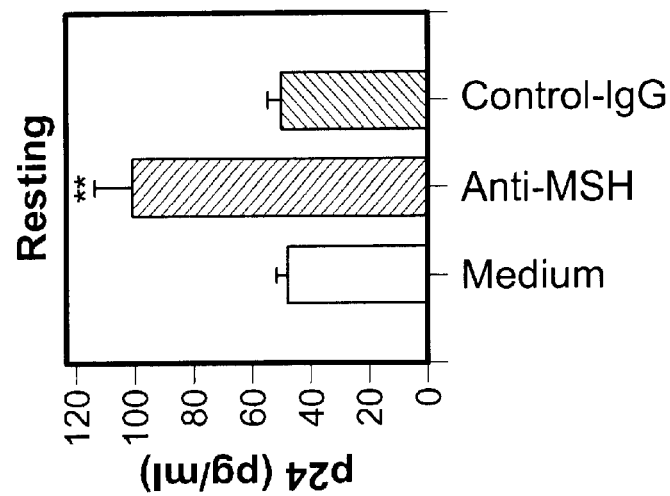

Influence of Endogenous α-MSH on HIV Expression in Chronically Infected U1 Cells α-MSH receptor MC-1R gene expression was determined in resting and PMA-stimulated U1 cells. In both conditions, a PCR product specific for MC-IR with the expected length of 416 bp was detected (FIG. 1). Supernatants of resting and stimulated U1 cells were analyzed for production of α-MSH. There was a small but consistent production of peptide after 48 h culture in unstimulated conditions (5.2±0.3 pmol/mL). When cells were coincubated with PMA, α-MSH in the supernatants was increased to 12.90±0.42 pmol/mL. To determine effects of blockade of endogenous α-MSH on HIV-replication, the peptide was immunoneutralized with a specific anti-α-MSH antibody. p24 antigen was measured in the supernatants from resting cells and from those exposed to PMA or in crowding conditions. In cells incubated with the anti-α-MSH antibody there was a substantial increase in p24 release under unstimulated and crowding conditions and after stimulation with PMA (FIG. 2). The irrelevant IgG did not alter p24 release in any condition.

Influence of α-MSH Peptides on HIV Expression in Chronically Infected UI Cells and in Acutely Infected MDM α-MSH [1–13] and the tripeptide KPV significantly inhibited p24 release from TNF-α-stimulated U1 cells (FIG. 3). Inhibitory effects of α-MSH occurred over a broad range of peptide concentrations including picomolar concentrations that occur in human plasma (12). These peptide concentrations significantly inhibited p24 release (34–36%), suggesting that the small amounts of endogenous α-MSH present in the circulation can inhibit HIV expression. Greater concentrations caused more pronounced HIV inhibition, with the most effective concentration for both peptides being $10^{-5}$ M. In this concentration, α-MSH [1–13] and KPV caused 52.7% and 56.0% inhibition of p24 release, respectively. In subsequent experiments the highly effective $10^{-5}$ M concentration was used to determine any influence of KPV on p24 release induced by different stimuli.

On the basis of these parallel effects and because KPV possesses advantages over α-MSH [1–13] in terms of cost and absorption, further tests on HIV replication were based on KPV.

KPV significantly inhibited p24 and RT release from U1 cells induced by IL-6, IL-10, PMA, and in crowding condition (FIG. 4).

The inhibitory activity of KPV on HIV expression was confirmed by Northern blot analysis of HIV-RNA in PMA-stimulated U1 cells (FIG. 5). Addition of KPV reduced by approximately 50% both spliced and unspliced HIV-1 RNA in PMA-stimulated U1 cells.

U1 cells are an in vitro model of latent HIV infection in which induction of viral replication does not lead to production of infecting virus. Therefore, the effects of KPV were also investigated in acutely infected MDM, which are a more realistic model of productive HIV-infection. Treatment with the tripeptide significantly inhibited RT release in acutely infected MDM (FIG. 6). Inhibitory effect was more pronounced on day 6 but was still statistically significant on day 2 1.

NF-κB DNA-binding Activity in U1 Cells

Because NF-κB is a central mediator in cytokine activation of HIV transcription the effect of KPV on NF-κB DNA binding in U1 cells was determined. TNF-α treatment greatly enhanced NF-κB DNA-binding activity and coincubation of cells with $10^{-5}$ M peptide significantly reduced NF-κB activation (FIG. 7). The tripeptide did not alter NF-κB activation in resting cells.

Discussion

Chronically HIV-1 infected promonocytic U1 cells express the gene for the α-MSH receptor MC-IR. Because resting and stimulated U1 cells produce α-MSH and immunoneutralization of the endogenous peptide enhances HIV expression, an autocrine inhibitory circuit based on α-MSH likely occurs in these cells. Treatment of U1 cells with the α-MSH peptides 1–13 and 11–13 KPV significantly reduces TNF-α-induced HIV-expression. Inhibitory influences occur over a very broad range of peptide concentrations, from picomolar to micromolar. The tripeptide KPV has effects similar to those of the larger α-MSH [1–13] sequence. Because the tripeptide possesses advantages over α-MSH in terms of cost and absorption, it was utilized in further tests on HIV expression in chronically and acutely infected cells. In U1 cells, KPV substantially inhibited HIV expression induced by both transcriptional-(TNF-α, PMA, crowding, IL-10) and post-transcriptional mechanisms (IL-6). Further, the tripeptide inhibited HIV replication in acutely HIV-infected MDM.

The presumed autocrine circuit for control of viral replication may be similar to that found in related studies. Activity of macrophages and glial cells can be modulated via an endogenous autocrine circuit that depends upon α-MSH and specific melanocortin receptors. Murine and human macrophages contain MRNA for the melanocortin receptor MC-IR and they secrete α-MSH. Blockade of endogenous α-MSH by immunoneutralization increased production of proinflammatory cytokines and nitric oxide in microglia. Incubation of resting macrophages with antibody to MC-IR promoted TNF-α production. Further, immunoneutralization of MC-IR markedly reduced the inhibitory influence of α-MSH on TNF-α production by activated macrophages. The present experiments in HIV-infected cells indicate that an autocrine circuit based on α-MSH likewise occurs in infected monocytes: U1 cells expressed MC-IR and produced α-MSH, and blockade of the endogenous peptide significantly enhanced HIV expression in both resting and stimulated cells. This suggests that endogendus α-MSH reduces viral expression via an autocrine mechanism. Such antiviral influences based on α-MSH could be significant to host protection. That is, in peripheral and central phagocytes, which are the main reservoir of the vius production, the action of α-MSH could reduce viral burden.

Further, when HIV-infected cells were incubated with low concentrations of α-MSH similar to those found in human plasma, there was substantial inhibition of HIV expression. This observation suggests that the endogenous peptide present in human plasma normally has anti-HIV effects. That circulating peptide exerts beneficial effects in HIV-infected patients is also suggested by previous research. Plasma concentrations of α-MSH are generally elevated in patients of the CDC groups III and IV and greater concentrations of α-MSH are associated with reduced disease progression or death. The correlation between elevated plasma α-MSH and reduced AIDS-related events supports the idea that the endogenous peptide tends to protect the host during HIV infection.

Replication of HIV is dependent on the state of activation of infected cells and is regulated by interactions between viral and host factors. Among the latter, proinflanmmatory cytokines have a prominent enhancing effect on HIV replication. TNF-α and other cytokines such as IL-1 and IL-6 promote HIV replication and have detrimental influences on HIV disease progression. Inhibition of such proinflammatory cytokines is, therefore, a target for adjunctive therapies of HIV infection. Endotoxin-stimulated production of IL-1, IL-6, and TNF-α in whole blood of HIV-positive patients was substantially reduced by α-MSH. Further, α-MSH inhibited TNF-α production by peripheral blood mononuclear cells stimulated with HIV envelope glycoprotein gp 120. α-MSH also reduced brain TNF-α in an in vivo model of brain inflammation. In addition to these cytokines, α-MSH inhibited several products of activated macrophages including neopterin and nitric oxide. The present results in chronically infected UI cells indicate that α-MSH peptides inhibit HIV replication induced by major stimuli known to up-regulate the virus in this cell model of chronic HIV infection.

One mechanism by which α-MSH regulates inflammatory reactions is through inhibition of IkBα degradation and reduction of the p65 subunit of NF-kB translocation to the nucleus. Activation of NF-kB plays a critical role in many aspects of cellular responses and is a primary target for the development of anti-inflammatory drugs. Therefore, α-MSH is a candidate for treatment of pathologic conditions in which activation of NF-kB is involved. HIV infection is clearly one such condition as NF-kB promotes transcription of HIV-1-LTR. Consistent with previous results in non-infected cells, the present data show that α-MSH inhibits NF-kB DNA binding also in UI cells.

UI cells are an in vitro model of latent HIV infection in monocytes in which HIV is present as two integrated proviral copies and constitutive expression is very low. Viral replication, which can be up-regulated by different stimuli, does not lead to production of infecting virus. Because of this difference from naturally infected phagocytes, the effects of KPV were also investigated in acutely HIV-infected MDM. In this model that represents more closely the circumstance in HIV infection, KPV substantially inhibited HIV replication.

EXAMPLE 1

A non-symptomatic patient. who has just been diagnosed with HIV desires immediate treatment to reduce initial proliferation of the virus. The patient's HIV status has been confirmed through Northern Blot testing and polymerase chain reaction testing. The patient is administered a therapeutic amount of KPV via injection or oral preparation. Therapeutic results are monitored via measurement of viral load and CD4 cell counts.

EXAMPLE 2

A previously non-symptomatic HIV positive patient has developed symptoms that may be signs of AIDS onset. The patient has contracted an upper respiratory tract infection that has been unresponsive to treatment. The patient desires to delay onset of AIDS and any accompanying secondary infections. The patient is administered a therapeutic amount of KPV via injection or oral preparation. Therapeutic results are monitored via measurement of viral load, CD4 cell counts, and clinical improvement.

EXAMPLE 3

A patient with fully symptomatic AIDS desires to improve clinically, reduce viral load and increase CD4 cell counts. The patient has developed pneumocystis carinii. The patient is administered a therapeutic amount of KPV via injection or oral preparation. Therapeutic effect is monitored by measuring viral load, CD4 cell counts, and clinical improvement.

II. Secondary Infections

The peptides used in this research included: α-MSH (1–13), (4–10), (6–13) and (11–13), all of which were N-acetylated and C-amidated and ACTH (1–39) and (18–39) (CLIP). Another peptide used in this research included a dimer of the amino acid sequence KPV, specifically VPKC-CKPV (SEQ ID NO: 4), which also was N-acetylated and C-amidated (the "KPV dimer"). The KPV dimmer can be chemically represented as $NH_2$-Val-Pro-Lys-Ac-Cys-Cys-Ac-Lys-Pro-Val-$NH_2$ (SEQ ID NO: 4) . The peptides were prepared by solid-phase peptide synthesis and purified by reversed-phase high performance liquid chromatography.

Organism and Culture Conditions

S. aureus (ATCC 29213) and C. albicans (clinical isolate) were obtained from the collection of the Department of Microbiology, Ospedale Maggiore di Milano. C. albicans were maintained on Sabouraud's agar slants and periodically transferred to Sabouraud's agar plates and incubated for 48 hours at 28° C. To prepare stationary growth phase yeast, a colony was taken from the agar plate and transferred into 30 ml Sabouraud-dextrose broth and incubated for 72 hours at 32° C. Cells were centrifuged at 100×g for 10 minutes and the pellet was washed twice with distilled water. Cells were counted and suspended in Hank's balanced salt solution ("HBSS") to the desired concentration. Viability, determined by the exclusion of 0.01% methylene blue, remained >98%.

Trial of Melanocortin Peptides on S. aureus Viability

S. aureus ($1 \times 10^6$/ml in HBSS) was incubated in the presence or absence of α-MSH (1–13) or (11–13) at concentrations in the range of $10^{-5}$ to $10^{-4}$M for two hours at 37° C. Cells were then washed in cold distilled water and diluted with HBSS to a concentration of 100 organisms/ml. One ml aliquots were dispensed on blood agar plates and incubated for 24 hours at 37° C. Organism viability was estimated from the number of colonies formed.

In experiments on S. aureus, we determined the influence of α-MSH on urokinase-induced growth-enhancement. Hart, D. A.; Loule, T.; Krulikl, W.; Reno, C., *Staphylococcus Aureus Strains Differ in Their in Vitro Responsiveness to Human Urokinase: Evidence that Methicillin-Resistant Strains are Predominantly Nonresponsive to the Growth-Enhancing Effects of Urokinase, Can. J. Microbiol.* 42, 1024–31 (1966). S. aureus ($10^5$/100 ml) were incubated for four hours at 37° C. with recombinant human urokinase 500 U (Lepetit, Milan, Italy) in a shaking waterbath, in the presence orabsence of α-MSH (1–13) or (11–13) $10^{-6}$M. Appropriate dilutions of S. aureus were dispensed on agar plates and colonies counted after 24 hours incubation at 37° C.

Trial of Melanocortin Peptides on C. albicans Viability

C. albicans ($1 \times 10^6$/ml in HBSS) was incubated in the presence or absence of α-MSH (1–13) or (11–13) at concentrations in the range of $10^{-15}$ to $10^{-4}$ M for two hours at 37° C. Cells were then washed in cold distilled water and diluted with HBSS to a concentration of 100 organisms/ml. One ml aliquots were dispensed on blood agar plates and incubated for 48 hours at 37° C. Organism viability was estimated from the number of colonies formed.

In subsequent experiments using similar procedures we compared activity of α-MSH (4–10), (6–13), (11–13), ACTH (1–39), (18–39), and fluconazole, the latter an established an agent. Melanocortin peptides and fluconazole were tested in concentrations of $10^{-6}$ to $10^{-4}$M. There were at least six replicates for each concentration of peptide.

Trial of α-MSH Peptides on C. albicans Germination

C. albicans from stationary phase cultures were washed twice with distilled water and suspended in HBSS to a final concentration of $2 \times 10^6$/ml. Hyphal growth was induced by addition of 10% inactivated horse serum (GMCO/BRL, Paisley, Great Britain) to yeast incubated for 45 minutes at 37° C. with continuous shaking. Horse serum was removed by washing cells twice with HBSS and incubation was continued for 60 minutes at 37° C. in the presence of α-MSH (1–13), (6–13) or (11–13) at a concentration of $10^{-4}$M with continuous shaking. The percentage of filamentous cells was evaluated under a light microscope with the aid of a hartocytometer. Experiments were run in triplicate and at least 200 cells were scored. Photomicrographs were taken with a MC100 carnera attached to an Axioskop Zeiss microscope.

Trial of α-MSH Peptides on C. albicans Killing by Human Neutrophils

Venous blood (20 ml) from healthy volunteers was anticoagulated with heparin. Neutrophils were isolated using dextran sedimentation and Ficoll-Hypaque (Sigma Chemical Co., St. Louis, Mo., USA) centrifugation. Erythrocytes were lysed via hypotonic shock. Neutrophils represented at least 97% of the cell suspension. Cell viability, estimated by trypan blue exclusion, was >98%. Neutrophils were suspended to final concentration in HBSS.

C. albicans ($1 \times 10^6$) were opsonized with human AB serum in a shaking water bath for 30 minutes at 37° C. Organisms were then incubated with neutrophils in presence of medium alone or medium with α-MSH (1–13) or α-MSH (11–13) in concentrations of $10^{-15}$ to $10^{-4}$ M in a shaking water bath for two hours at 37° C. After incubation, the culture tubes were placed on ice to stop growth and extracellular organisms were washed twice with centrifugation at 100×g at 4° C. A 2.5% sodium desoxycholate solution was added to the suspension and the tubes were shaken for five minutes. Cold distilled water was added to obtain a suspension of $10^6$ cells/ml. Two 1/100 serial dilution in HBSS were made to obtain a final suspension of 100 cells/ml. Aliquots of 1 ml were dispensed on blood agar plates and incubated for 48 hours at 37° C. Colony forming units ("CFU") were counted at the end of the incubation period. Experiments were run in triplicate and repeated using blood from five different donors.

Trial of α-MSH Peptides on cAMP Accumulations

C. albicans ($10^6$/ml), permeabilized with toluene/ethanol, were incubated at 37° C. with continuous shaking in the presence of $10^{-6}$M α-MSH (1–13), (11–13), forskolin, an agent known to increase intracellular cAMP, or in medium alone. The reaction was stopped after three minutes by the addition of ice cold ethanol. cAMP was measured in duplicate using a commercial enzyme immunoassay (EIA) kit (Amersham, United Kingdom) after extraction via the liquid-phase method according to manufacturer's instructions. The effect of forskolin ($10^{-4}$M) on C. albicans colony formation was determined using the same procedures as for α-MSH peptides.

Statistical Analysis

One-way analysis of variance and Student's t test were used to analyze the data. Probability values <0.05 were considered significant.

α-MSH Peptides Inhibited S. aureus Colony Formation

α-MSH peptides (1–13) and (11–13) inhibited S. aureus colony formation (FIG. 1). A dimer of the amino acid sequence KPV, specifically, $NH_2$-Val-Pro-Lys-Ac-Cys-Cys-Ac-Lys-Pro-Val-$NH_2$ (the "KPV dimer") (SEQ ID NO: 4) also inhibited S. aureus colony formation (FIG. 8). The inhibitory effect occurred over a wide range of concentrations and was significant (p<0.01) with peptide concentrations of $10^{-12}$ to $10^{-4}$M.

Treatment with urokinase increased S. aureus colony formation and addition of α-MSH (1–13) or (11–13) at concentrations of $10^{-6}$M significantly inhibited the enhancing effect of urokinase (FIG. 9).

α-MSH Peptides Inhibited *C. albicans* Colony Formation

*C. albicans* colony forming units ("CFU") were greatly reduced by α-MSH (1–13) and (11–13) (FIG. 10). A dimer of the amino acid sequence KPV, specifically, $NH_2$-Val-Pro-Lys-Ac-Cys-Cys-Ac-Lys-Pro-Val-$NH_2$ (the "KPV dimer") (SEQ ID NO: 4) also inhibited *C. albicans* colony formation (FIG. 10). Concentrations of all three peptides from $10^{-13}$ to $10^{-4}$M had significant inhibitory influences on CFU ($p<0.01$ vs. control).

In experiments comparing the relative potency of $10^{-4}$M melanocortin peptides in reducing *C. albicans* viability, α-MSH (11–13), (6–13) and (1–3) were the most effective (FIG. 11). Their inhibitory activity was similar to that of equimolar fluconazole. The "core" α-MSH sequence (4–10), which has behavioral effects but little anti-inflamatory activity, caused approximately 50% inhibition of CFU. Although this inhibitory effect was substantial ($p<0.01$ vs. control), it was significantly less than that caused by α-MSH fragments bearing the KPV signal sequence, i.e., α-MSH (6–13) and (11–13) ($p<0.01$), or the parent molecule α-MSH (1–13) ($p<0.05$). ACTH (1–39) and the ACTH fragment (18–39) did not reduce *C. albicans* viability (FIG. 11). Even higher concentrations of these ACTH peptides (up to $10^{-4}$M) were likewise ineffective in reducing *C. albicans* CFU (results not shown in the figures).

α-MSH Peptides Reduced *C. albicans* Germination

Coincubation of *C. albicans* with α-MSH (1–13) or (11–13) inhibited germ tube formation induced by horse serum (FIGS. 5A–D), α-MSH (1–13) caused 28–32% reduction in the number of filamentous cells; the tripeptide inhibited germination by 54–58%. The octapeptide α-MSH (6–13) had similar activity (approximately 50% inhibition) (not shown).

α-MSH Peptides Enhanced *C. albicans* Killing by Human Neutrophils

α-MSH (1–13) and (11–13) enhanced killing of *C. albicans* by human neutrophils when administered in concentrations of $10^{-12}$ to $10^{-4}$ ($p<0.01$) (FIG. 13). Therefore, enhanced killing occurred over a very broad range of concentrations including picomolar concentrations, i.e., the quantity of α-MSH found in human plasma. Catania, A; Airaghi, L.; Garofalo, L.; Cutuli, M.; Lipton, J. M., *The Neuropeptide α-MSH in AIDS and Other Conditions in Humans*, Ann. N.Y. Acad. Sci. 840, 848–856 (1998).

α-MSH Peptides Increased cAMP Accumulation

Because many of the effects of α-MSH are known to be mediated by induction of cAMP, measurements of the effects of α-MSH peptides on cAMP accumulation in *C. albicans*. α-MSH (1–13) and (11–13) enhanced cAMP content in the yeast (FIG. 14). The increase was of the same order of magnitude as that induced by equimolar forskolin, an adenylate cyclase activator (FIG. 14). To determine whether increases in cAMP could be responsible for reduction in CFU, we tested the effects of forskolin on *C. albicans* viability. Results showed that $10^{-4}$ forskolin markedly inhibited *C. albicans* CFU relative to control ($p<0.01$). The inhibitory effect was similar to that exerted by α-MSH peptides (FIG. 15).

III. Discussion

Antimicrobial Agents Against the Viability of Microbes

The results show that α-MSH (1–13), its C-terminal tripeptide (11–13), and other α-MSH fragments have significant antimicrobial effects against at least two major pathogens: *S. aureus* and *C. albicans*. The most effective of the α-MSH peptides were those including the C-terminal amino acid sequence KPV of the α-MSH sequence, i.e., α-MSH (1–13), (6–13) and (11–13). A dimer of the amino acid sequence KPV, specifically, VPKCCKPV (SEQ ID NO: 4) (referred to herein as the "KPV dimer," shown in FIG. 16) has also been shown to be at least as effective as α-MSH (11–13) against microbes. The α-MSH "core" sequence (4–10), which is known to influence learning and memory, but has little antipyretic and anti-inflammatory influence, was effective, but less so. The ACTH peptides (1–39) and (18–39) did not have significant candidacidal effects. These observations indicate that antimicrobial activity is not common to all melanocortin peptides, but rather that it is specific to α-MSH amino acid sequences, and most particularly to the C-terminal amino-acid sequences of α-MSH.

The antimicrobial effects of these α-MSH peptides occurred over a very broad range of concentrations, including picomolar concentrations that normally occur in human plasma. Catania, A.; Airaghi, L.; Garofalo, L.; Cutuli, M.; Lipton, J. M., *The Neuropeptide α-MSH in AIDS and Other Conditions in Humans*, Ann. N.Y Acad. Sci. 840, 848–856 (1998). This suggests that endogenous α-MSH has a physiological role in natural immunity.

Therefore, these α-MSH peptides are expected to be useful as a broad prophylactic against microbial infection and in the treatment of human and veterinary disorders resulting from microbial invasion. Further, these peptides that likewise have anti-inflammatory activity could be used to treat cases in which both inflammation and microbial invasion coexist, or where the aim is to prevent their coexistence or development.

Antimicrobial Agents Against Germination of Yeasts

Yeasts can be major pathogens. For example, *C. albicans* is the leading cause of invasive fungal disease in patients with HIV or other immunosuppressed conditions, premature infants, diabetics, and surgical patients. Despite appropriate therapy, death resulting from systemic *C. albicans* infection in immunocompromised patients is substantial. Wenzel, R. P., Pfaller, M. A., *Candida Species: Emerging Hospital Bloodstream Pathogens*. Infect. Control. Hosp. Epidemiol. 12, 523–4 (1991); Cartledge, J. D., Midgley, J., Gazzard, B. G., *Clinically Significant Azole Cross-Resistance in Candida Isolates from HIV-Positive Patients with Oral Candidosis*, AIDS 11, 1839–44 (1997). The pathogenesis of *C. albicans* infection involves adhesion to host epithelial and endothelial cells and morphologic switching of yeast cells from the ellipsoid blastospore to various filamentous forms: germ tubes, pseudohyphae, and hyphae. Gow, N. A., *Germ Tube Growth of Candida Albicans*, Curr. Topics Med. Mycol. 8, 43–55 (1997). It is therefore important that α-MSH (1–13) and its C-terminal tripeptide (11–13) not only reduce the viability of yeast, but also reduce germination of yeast.

Antimicrobial and Anti-inflammation Effects Without Reducing Killing by Human Neutrophils Reduced killing of pathogens is a dire consequence-of therapy with corticosteroids and nonsteroidal anti-inflammatory drugs during infection. Steven, D. L., *Could Nonsteroidal Anti-inflammatory Drugs (NSAIDs) Enhance Progression of Bacterial Infections to Toxic Shock Syndrome?*, Clin. Infect. Ids 21, 977–80 (1995); Capsoni. F.; Merino, P. L.; Zocchi, M. R.; Plebani, A. M.; Vezio, M., *Effect of Corticosteroids on Neutrophil Function: Inhibition of Antibody-Dependent Cell-Mediated Cytoxicity (ADCC)*, J. Immunopharmacol. 5, 217–30 (1983). This effect could be particularly dangerous in the immunocompromised host.

α-MSH has potent anti-inflanunatory influences in models of acute, chronic, and systemic inflammation. Its wide spectrum of activity and low toxicity suggest that α-MSH is useful for treatment of inflammation in human and veterinary disorders. It was, therefore, important to learn the influence of α-MSH peptides on *C. albicans* killing by phagocytes. This is especially important because α-MSH is knownto inhibit neutrophil chemotaxis. Catania, A.; Rajora, N.; Capsoni, F.; Minonzio, F.; Star, R. A.; Lipton, J. M., *The Neuropeptide α-MSH has Specific Receptors on Neutro hils and Reduces Chemotaxis in Vitro, Peptides* 17, 675–679 (1996). In the absence of trial, it could have been expected to reduce killing by human neutrophils, despite the direct antimicrobial effect. Results of the present research indicate that α-MSH peptides do not reduce killing but rather enhance it, likely as a consequence of the direct candidacidal effect. Therefore, anti-inflammnatory agents such as α-MSH peptides that have antimicrobial effects are expected to be very useful in clinical practice.

Theoretical Discussion and cAMP Accumulation

An important question concerns how α-MSH peptides exert their antimicrobial effects and whether they operate like other natural antimicrobial agents.

It is known that α-MSH shares a number of similarities with other natural antimicrobial peptides such as the defensins or the cathelicidins:

1) It is produced in mammals but also in primitive organisms that lack adaptive immunity. Eberle, A. N., *The Melanotronins*, Karger, Basel, Switzerland (1988).

2) Like known antimicrobial peptides, its precursor molecule proopiomelanocortin (POMC) is expressed in phagocytes and epithelia and post-translational proteolytic processing is required to convert it to active α-MSH. Rajora, N.; Ceriani, G.; Catania, A.; Star, R. A.; Murphy, M. T.; Lipton, J. M., *α-MSH Production, Receptors, and Influence on Neopterin in a Human Monocyte/Macrophage Cell Line J. Leukoc. Biol.* 59, 248–253 (1996); Luger, T. A.; Schauer, E.; Trautinger, F.; Krutmann, J.; Ansel, J.; Schwarz, A.; Schwartz, T., *Production of Immunosuppressing Melanotropins by Human Keratinocytes Ann. M. Y. Acad. Sci.* 680, 567–570 (1993);

3) It is a cationic peptide.

4) it has antimcrobial influences against at least two disparate pathogens, a yeast and a bacterium. In addition, α-MSH inhibits HIV-1 replication in acutely and chronically infected monocytes. These findings indicate that α-MSH has the broad spectrum of activity of other innate antimicrobial substances.

The mechanism of action of natural antimicrobial agents is only partly understood. Most of these peptides, including the defensins, alter membrane permeability and impair internal homeostasis of organism. The first contact is made between the cationic groups of the peptide and the negatively charged head of the target membrane. Then, the tertiary structure determines the mode of insertion of the peptide into membranes where they form ion channels or pores that disrupt cell integrity. It is known that cAMP-enhancing agents inhibit mRNA and protein synthesis in *C. albicans*. Bhattachaaya, A.; Datta, A., *Effect of Cyclic AMP on RNA and Protein Synthesis in Candida Albicans*, Biochem. Biophys. Res. Commun., 77:1483–44 (1977).

In the present experiments, it is shown that α-MSH induces cAMP accumulation in *C. albicans* and also that the cAMP-inducing agent forskolin inhibited colony formation. Without being limited by this theoretical explanation, it may be that the antimicrobial effect was caused by enhancement of this mediator.

Biologically Functional Equivalents

As used herein, a biological functional equivalent is defined as an amino acid sequence that is functionally equivalent in terms of biological activity.

Although the specific amino acid sequences described here are effective, it is clear to those familiar with the art that amino acids can be substituted in the amino acid sequence or deleted without altering the effectiveness of the peptides. Further, it is known that stabilization of the α-MSH sequence can greatly increase the activity of the peptide and that substitution of D-amnino acid forms for L-forms can improve or decrease the effectiveness of peptides. For example, a stable analog of α-MSH, [Nle$^4$, D-Phe$^7$], α-MSH, which is known to have marked biological activity on melanocytes and melanoma cells, is approximately ten times more potent than the parent peptide in reducing fever. Holdeman, M. and Lipton, J. M., *Antipyretic Activity of a Potent α-MSH Analog, Peptides* 6, 273–5 (1985). Further, adding amino acids to the C-terminal α-MSH (11–13) sequence can reduce or enhance antipyretic potency (Deeter, L. B.; Martin, L. W.; Lipton, J. M., *Antipyretic Properties of Centrally Administered α-MSH Fragments in the Rabbit*, Peptides 9, 1285–8 (1989). Addition of glycine to form the 10–13 sequence slightly decreased potency; the 9–13 sequence was almost devoid of activity, whereas the potency of the 8–13 sequence was greater than that of the 11–13 sequence. It is known that Ac-[D-K$^{11}$] α-MSH 11–13-NH$_2$ has the same general potency as the L-form of the tripeptide α-MSH 11–13. Hiltz, M. E.; Catania, A.; Lipton, J. M., *Anti-inflammatory Activity of α-MSH* (11–13) *Analogs: Influences of Alterations in Stereochemistry*, Peptides 12, 767–71 (1991). However, substitution with D-proline in position 12 of the tripeptide rendered it inactive. Substitution with D-proline in position 12 of the tripeptide rendered it inactive. Substitution with the D-form of valine in position 13 or with the D-form of lysine at position 11 plus the D-form of valine at position 13 resulted in greater anti-inflammatory activity than with the L-form tripeptide. These examples indicate that alterations in the amino acid characteristics of the peptides can influence activity of the peptides or have little effect, depending upon the nature of the manipulation.

It is also believed that biological functional equivalents may be obtained by substitution of amino acids having similar hydropathic values. Thus, for example, isoleucine and leucine, which have a hydropathic index +4.5 and +3.8, respectively, can be substituted for valine, which has a hydropathic index of +4.2, and still obtain a protein having like biological activity. Alternatively, at the other end of the scale, lysine (−3.9) can be substituted for arginine (−4.5), and so on. In general, it is believed that amino acids can be successfully substituted where such amino acid has a hydropathic score of within about +/−1 hydropathic index unit of the replaced amino acid.

EXAMPLE 1

A female patient with symptomatic HIV complains to her doctor about vaginal discharge and itching. She is diagnosed with a *Candida albicans* infection, secondary to HIV. She desires clinical improvement. A therapeutic amount of KPV is administered topically in the form of a cream. Therapeutic effect is measured by clinical improvement of the discharge and itching.

EXAMPLE 2

A hospitalized patient with symptomatic HIV develops a systemic infection with *Candida albicans* from catheters used during the hospitalization. The patient desires clinical improvement. A therapeutic amount of KPV is administered in the form of an injection or oral preparation. Therapeutic effect is measured by clinical improvement and blood analysis for the presence of candida.

EXAMPLE 3

A patient with symptomatic HIV develops a secondary infection with *Staphylococcus aureus* that is localized to a single skin lesion. The patient desires clinical improvement. A therapeutic amount of KPV is administered topically in the form of a cream. Therapeutic effect is measured by clinical improvement.

EXAMPLE 4

A patient hospitalized with HIV develops a systemic infection with *Staphylococcus aureus*. The patient desires clinical improvement. A therapeutic amount of KPV is administered in the form of an injection or oral preparation. Therapeutic effect is measured by clinical, improvement and blood analysis for the presence of *S. aureus*.

EXAMPLE 5

A patient with HIV develops a systemic infection with both *Staphylococcus aureus* and *Candida albicans*. The patient desires clinical improvement. A therapeutic amournt of KPV is adniinistered in the form of an injection or oral preparation. Therapeutic effect is measured by clinical improvement and blood analysis for the presence of *S. aureus* and *Candida albicans*.

Polypeptides that include an amino acid sequence from the group consisting of KPV, MEHFRWG (SEQ ID NO: 1), HFRWGKPV (SEQ ID NO: 2), and SYSMEHFRWGKP (SEQ ID NO: 3) are useful in pharmaceutically acceptable oral, parenteral or topical modes. These pharmaceutical compositions contain an amino acid sequence from the group consisting of KPV, MEHFRWG (SEQ ID NO: 1), HFRWGKPV, (SEQ ID NO: 2), and SYSMEHFRWGKP (SEQ ID NO: 3) in association with a compatible pharmaceutically acceptable carrier material. Any conventional carrier material can be utilized. The carrier can be organic or an inert inorganic carrier. For oral use, the carrier may be water, gelatin, gum arabic, lactose, starch, magnesium stearate, talc, vegetable oils, polyalkylene-glycols, petroleum jelly and the like. Additional additives, such as flavorings, preservatives, stabilizers, emulsifiers, buffers and the like may be added in accordance with accepted practices of pharmaceutical compounding.

The pharmaceuticals may be administered either orally, parenterally, or by local application to specific areas affected by *C. albicans, S. aureus* or other bacteria and/or fungi. Oral preparations include solid forms of administration, such as tablets, granules, capsules, pills and the like. Topical pharmaceuticals include solutions, suspensions, ointments, creams, powders, gels, aerosols and the like. Injectible solutions with carriers such as saline may also be used. Inhalers may also be used to deliver the polypeptides in the pharmaceuticals. The pharmaceutical preparations may be sterilized and/or may contain adjuvants, such as preservatives, stabilizers, wetting agents, emulsifiers, salts for varying the osmotic pressure and/or buffers.

For oral administration, tablets, capsules of hard or soft gelatin methylcellulose or of another suitable material easily dissolved in the digestive tract may be used. Oral dosages for the present invention will vary in accordance with the needs of the individual patient as determined by the prescribing physician. Generally, a daily oral dosage of about 1–10 milligrams/kg orally or 1–10 micrograms/kg intravenously is preferred. The dosage may be administered four times per day orally or up to 10 micrograms/kg/hour if given intravenously.

Topical administration to the skin may be in the form of ointments, creams, gels, solutions, lotions, sprays, suspensions and the like. The active ingredient can be mixed with a non-toxic, therapeutically inert, solid or liquid carrier customarily used in such preparations. It is preferred that these compounds contain about 10–40 percent of the active peptide by weight. It is also preferred that these preparations be applied up to four times daily to the skin. Preservatives, thickeners, perfumes and the like may be added to the topical preparations.

Ointment formulations containing an active agent in accordance with this invention comprise admixtures of a semi-solid petroleum hydrocarbon with a solvent dispersion of the active material. Cream compositions containing the active ingredient for use in this invention preferably comprise emulsions formed from a water phase of a humectant, a viscosity stabilizer and water, an oil phase of a fatty acid alcohol, a semi-solid petroleum hydrocarbon and an. emulsifying agent and a phase containing the active agent dispersed in an aqueous stabilizer-buffer solution.

Topical carriers can be applied to the site of the infection or inflammation by an applicator such as a syringes or syringe like apparatus, bandages, catheters, tubes with a plunger, spatula or other types of flat surface applicators.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

---

Having described the invention, what is claimed is:

1. A method for inhibiting opportunistic infections in an HIV-infected individual comprising: administering to the individual a pharmaceutically appropriate amount of a KPV tripeptide.

2. The method of claim 1, wherein the KPV tripeptide is contained in a carrier selected from the group consisting of a solution for injection, a liquid, a pill, a capsule, a cream, an ointment, a gel, a suppository, an aerosol spray, and an inhaler.

3. A method for inhibiting opportunistic infections in an HIV-infected individual comprising: administering a KPV tripeptide composition in a pharmaceutically appropriate amount to the HIV-infected individual wherein the KPV tripeptide composition comprises the KPV tripeptide and a carrier.

4. The method of claim 3, wherein the KPV tripeptide composition is administered orally, parenterally, locally or topically.

5. The method of claim 3, wherein the carrier is water, saline, gelatin, gum arabic, lactose, starch, magnesium stearate, talc, vegetable oil, polyalkylene-glycol, petroleum jelly, a solution, a suspension, an ointment, a cream, a powder, a gel, or an aerosol.

6. The method of claim 3, wherein the KPV composition further comprises an additive.

7. The method of claim 6, wherein the additive is a flavoring, a preservative, a stabilizer, a emulsifier, a buffer or a combination thereof.

8. The method of claim 3, wherein the pharmaceutically appropriate amount for an oral administration is about 1–10 milligrams/kg.

9. The method of claim 3, wherein the pharmaceutically appropriate amount for an intravenous administration is about 1–10 micrograms/kg.

10. The method of claim 3, wherein the KPV tripeptide composition comprises 10–40% by weight of the KPV tripeptide composition for a topical administration.

11. A method for inhibiting bacterial or fungal infections in an HIV-infected individual comprising administering to the HIV-infected individual a pharmaceutically appropriate amount of a KPV tripeptide.

12. The method of claim 11, wherein the KPV tripeptide is contained in a carrier selected from the group consisting of a solution for injection, a liquid, a pill, a capsule, a cream, an ointment, a gel, a suppository, an aerosol spray, and an inhaler.

13. A method for inhibiting bacterial or fungal infections in a-an HIV-infected individual comprising: administering a KPV tripeptide composition in a pharmaceutically appropriate amount to the HIV-infected individual, wherein the KPV tripeptide composition comprises a KPV tripeptide and a carrier.

14. The method of claim 13, wherein the KPV tripeptide composition is administered orally, parenterally, locally or topically.

15. The method of claim 13, wherein the carrier is water, saline, gelatin, gum arabic, lactose, starch, magnesium stearate, talc, vegetable oil, polyalkylene-glycol, petroleum jelly, a solution, a suspension, an ointments a cream, a powder, a gel, or an aerosol.

16. The method of claim 13, wherein the KPV tripeptide composition further comprises an additive.

17. The method of claim 16, wherein the additive is a flavoring, a preservative, a stabilizer, a emulsifier, a buffer or a combination thereof.

18. The method of claim 13, wherein the pharmaceutically appropriate amount for an oral administration is about 1–10 milligrams/kg.

19. The method of claim 13, wherein the pharmaceutically appropriate amount for an intravenous administration is about 1–10 micrograms/kg.

20. The method of claim 13, wherein the KPV tripeptide in the KPV tripeptide composition comprises 10–40% by weight of the KPV tripeptide composition for a topical administration.

* * * * *